United States Patent
Chow et al.

(12)

(10) Patent No.: US 6,498,497 B1
(45) Date of Patent: Dec. 24, 2002

(54) MICROFLUIDIC CONTROLLER AND DETECTOR SYSTEM WITH SELF-CALIBRATION

(75) Inventors: Calvin Y. H. Chow, Portola Valley; Morten J. Jensen, San Francisco; Colin B. Kennedy, Mill Valley; Michael M. Lacy, Ben Lomond; Robert E. Nagle, Mountain View, all of CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/374,878

(22) Filed: Aug. 13, 1999

Related U.S. Application Data

(60) Provisional application No. 60/104,260, filed on Oct. 14, 1998.

(51) Int. Cl.[7] .......................... G01R 35/00; G01R 27/02
(52) U.S. Cl. ........................................ 324/601; 324/607
(58) Field of Search ................................. 324/601, 649, 324/74, 650, 76.23; 702/85

(56) References Cited

U.S. PATENT DOCUMENTS 5,621,329 A * 4/1997 Tsao et al. .................. 324/601

* cited by examiner

*Primary Examiner*—N. Le
*Assistant Examiner*—James Kerveros
(74) *Attorney, Agent, or Firm*—Ritter, Lang & Kaplan LLP

(57) ABSTRACT

A microfluidic controller and detector system and method for performing screening assays are disclosed. The microfluidic controller and detector system comprises a fluidic chip that includes at least two intersecting channels and a detection zone, a fluid direction system comprising an electrical interface configured for electrical contact with the at least two intersecting channels, an optics block having an objective lens disposed adjacent the detection zone, and a control system coupled to the optics block and adapted to receive and analyze data from the optics block. The electrical interface generally includes electrodes configured for electrical contact with the intersecting channels and coupled to electrode channels for supplying electrical input to the electrodes. A reference channel is optionally provided to calibrate the electrode channels.

14 Claims, 42 Drawing Sheets

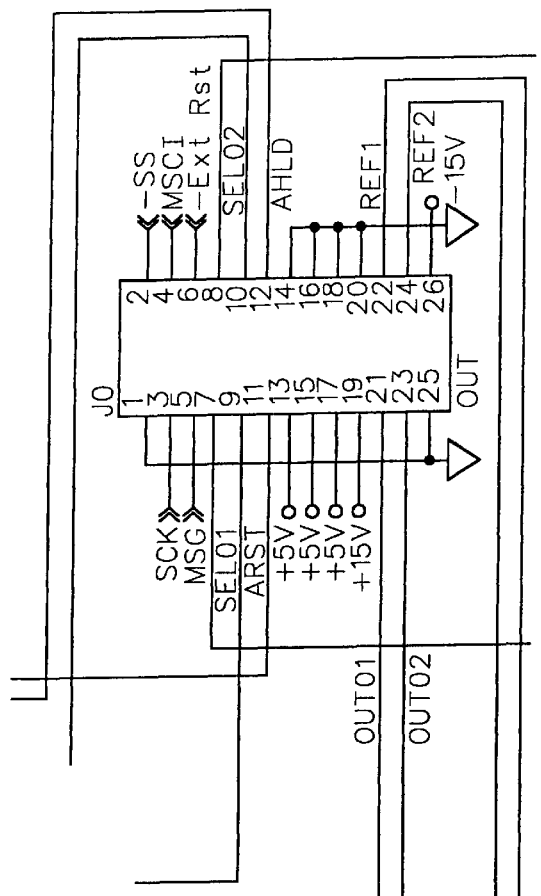
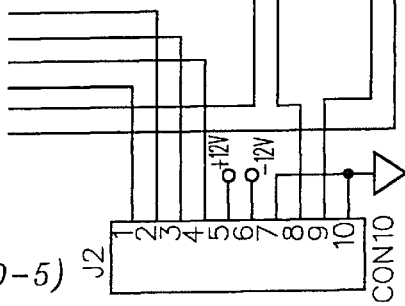
FIG. 4D-6

(SEE FIG. 4D-8)
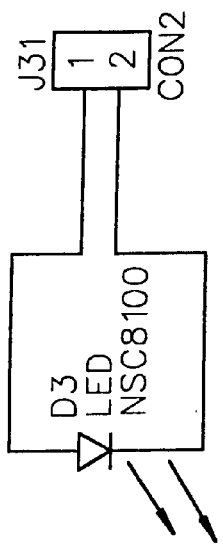
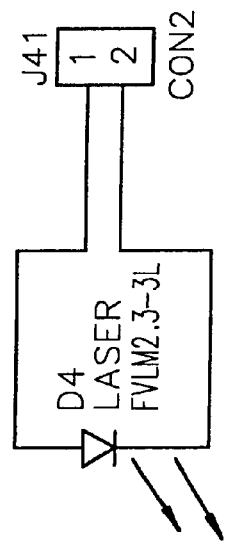
(SEE FIG. 4D-5)
FIG. 4D-7

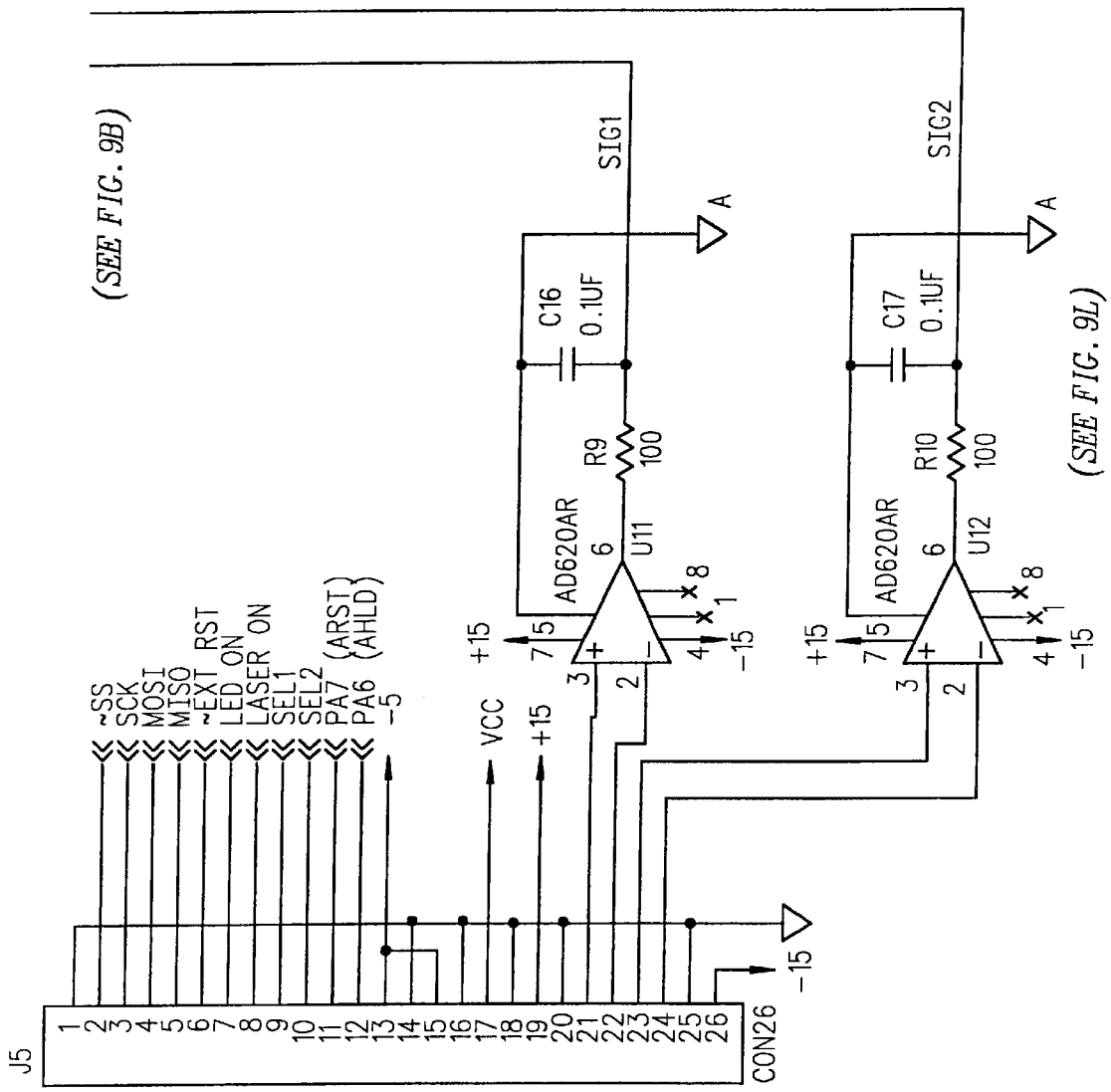

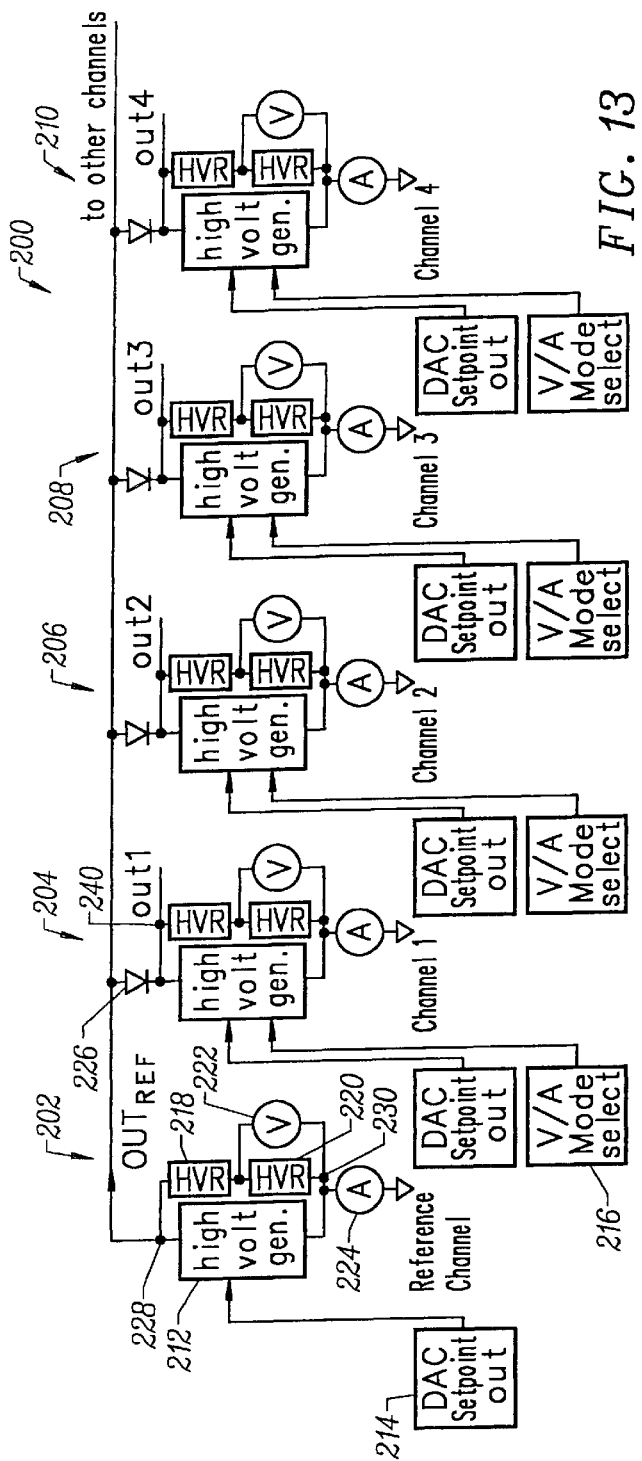
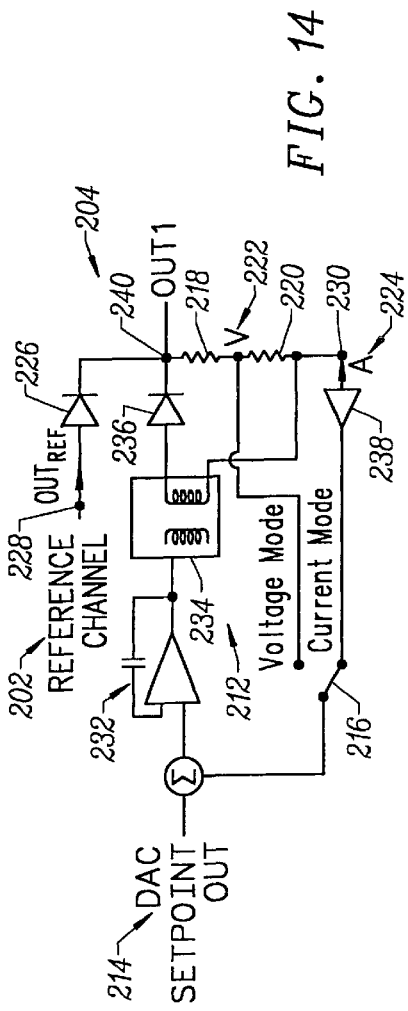
FIG. 13
FIG. 14

MICROFLUIDIC CONTROLLER AND DETECTOR SYSTEM WITH SELF-CALIBRATION

CROSS REFERENCE TO RELATED APPLICATION

This application claims priority to U.S. Provisional Patent Application Serial No. 60/104,260, entitled "Microfluidic Controller/Detector Apparatus and Method of Use Thereof" and filed on Oct. 14, 1998, the entirety of which is incorporated herein by reference.

BACKGROUND OF THE INVENTION

The present invention relates to a controller and detector system for microfluidic systems, and more particularly, to a microfluidic controller and detector system for use with assay systems for performing chemical and biochemical analyses.

Analysis of chemical and biochemical samples often requires detection and identification of the constituent elements of the sample. Microfluidic devices are often used to separate and control movement of the elements of the sample to detect a property of the elements with a detection system. Microfluidics technology moves small volumes of fluids through channels on a chip to perform a multitude of laboratory tests to obtain biochemical and chemical information. This laboratory-on-a-chip technology enables microfluidics systems to support a range of applications in drug discovery, bioanalytical research and medical diagnostics, including DNA, RNA, and cell analyses.

The microfluidic devices typically include multiple wells that are interconnected with microchannels for transport of the sample. Application of a voltage across the channels permits the electrophoretic migration of macromolecular species in the sample. The samples often include an intercalating dye that becomes more fluorescent upon binding to the species of the sample. The fluorescent dyes are used to identify and locate a variety of cell structures such as specific chromosomes within a DNA sequence.

A variety of devices have been designed to read fluorescent labeled samples. In general the devices include at least one light source emitting light at one or more excitation wavelengths and a detector for detecting one or more fluorescent wavelengths. The light source is often a laser that emits light at one narrow center wavelength (single mode laser).

Despite the improvements achieved using parallel screening methods and other technological advances, such as robotics and high throughput detection systems, current screening methods still have a number of associated problems. For example, screening large numbers of samples using existing parallel screening methods have high space requirements to accommodate the samples and equipment, e.g., robotics etc., high costs associated with that equipment, and high reagent requirements necessary for performing the assays. Additionally, in many cases, reaction volumes must be very small to account for the small amounts of the test compounds that are available. Such small volumes compound errors associated with fluid handling and measurement, e.g., due to evaporation, small dispensing errors, or the like. Additionally, fluid handling equipment and methods have typically been unable to handle these volume ranges within any acceptable level of accuracy due in part to surface tension effects in such small volumes.

What is desirable is an integrated system to increase productivity, increase time- and cost-efficiency, rendering conventional laboratory procedures less cumbersome, less labor-intensive and less expensive and requiring fewer highly trained personnel.

SUMMARY OF THE INVENTION

The present invention provides a microfluidic controller and detector system. The controller and detector system is typically configured to receive a fluidic chip including at least two intersecting channels. The system preferably includes a detection zone and a material direction system comprising an interface configured for contact with the at least two intersecting channels on a different side of an intersection formed by the at least two intersecting channels. The microfluidic controller and detector optionally further includes an optics block comprising an objective lens and is located within the housing adjacent the detection zone. Finally, the microfluidic controller and detector typically includes a control system coupled to the microfluidic controller and detector with a communication channel for controlling operation of the microfluidic controller and detector. The control system is configured for receiving and analyzing data from the optics block.

The microfluidic controller and detector system generally comprises a fluidic chip that includes at least two intersecting channels and a detection zone, a material direction system comprising an interface configured for contact with the at least two intersecting channels, an optics block having an objective lens disposed adjacent the detection zone, and a control system coupled to the optics block and adapted to receive and analyze data from the optics block. The interface may be an electrical interface and/or a vacuum port adapted for interface with a vacuum pump.

In one embodiment, the electrical interface optionally comprises at least three electrodes, each configured for electrical contact with one of the intersecting channels on a different side of an intersection formed by the intersecting channels. In another embodiment, the material direction system includes a lid connected to the electrodes such that when the lid is in a closed position, the electrodes are in electrical contact with the intersecting channels. In yet another embodiment, the electrical interface also includes a reference voltage source for calibrating the channel electrodes. In yet another embodiment, the interface to the fluidic chip includes a vacuum port for moving a material, such as fluids and/or charged chemical species, using vacuum or pressure.

Preferably, the optics block includes a light detector to detect light emitting from the detection zone via the objective lens. The light detector is typically selected from photodiode, avalanche photodiode, photomultiplier tube, diode array, imaging systems, and charged coupled devices. In one embodiment, the light detector is in communication with the control system. The optics block optionally further includes a detector lens assembly positioned adjacent the light detector through which light from the detection zone travels. In addition, the optics block optionally includes a light source operable to direct light toward the detection zone via the objective lens and a mirror that reflects light produced by the light source and transmits light emitted from the detection zone via the objective lens. The light source is typically a laser, a laser diode, or a light emitting diode.

In another embodiment, the microfluidic controller and detector system includes a mounting apparatus for focusing light from the light source onto the detection zone via the objective lens. The mounting apparatus preferably comprises a first and a second adjacent plate, a pivot, and an actuator for displacing the first plate relative to the second plate about the pivot. The mounting apparatus typically includes two actuators each for displacing the first plate relative to the second plate in a different direction about the pivot. The actuator preferably is a stepper motor coupled to a coupler, the coupler being coupled to the first plate and in movable contact with the second plate. In one embodiment, the coupler defines threads therearound and the first plate defines an orifice therethrough, the orifice having internal threads configured to engage the threads of the coupler. Preferably, the second plate includes a hard seat adapted to be in contact with the coupler.

According to another embodiment, a method of calibrating a plurality of electrical source channels generally comprises generating a first electrical reference input at a reference channel and a first electrical source input at each of the electrical source channels, measuring a first electrical value at each of the reference and electrical source channels, generating a second electrical reference input at the reference channel and a second electrical source input at each of the electrical source channels, the second electrical reference input and the second electrical source input being different from the first electrical reference input and the first electrical source input, respectively, measuring a second electrical value at each of the reference and electrical source channels, and determining a readout calibration factor as a function of a ratio of differences between the first measured reference value and the first measured source value and between the second measured reference value and the second measured source value.

The above is a brief description of some features and advantages of the present invention. Other features, advantages, and embodiments of the invention will be apparent to those skilled in the art from the following description, drawings, and claims.

BRIEF DESCRIPTION OF THE DRAWINGS

The present invention will be readily understood by the following detailed description line conjunction with the accompanying drawings, wherein like reference numerals designate like structural elements, and in which:

FIG. 13 is a simplified schematic illustrating one embodiment of circuitry for a high voltage control PCB assembly of a reference channel and various high voltage electrode channels for use with the microfluidic controller and detector system illustrated in FIGS. 1A and 1B; and FIG. 14 is a simplified schematic of circuitry for a high voltage loop for use as the reference channel or one of the high voltage electrode channels in the microfluidic controller and detector system illustrated in FIGS. 1A and 1B.

DETAILED DESCRIPTION OF THE PREFERRED EMBODIMENTS

A microfluidic controller and detector with self-calibration are disclosed. The following description is presented to enable any person skilled in the art to make and use the invention. Descriptions of specific embodiments and applications are provided only as examples and various modifications will be readily apparent to those skilled in the art. The general principles defined herein can be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

Figure 1A:
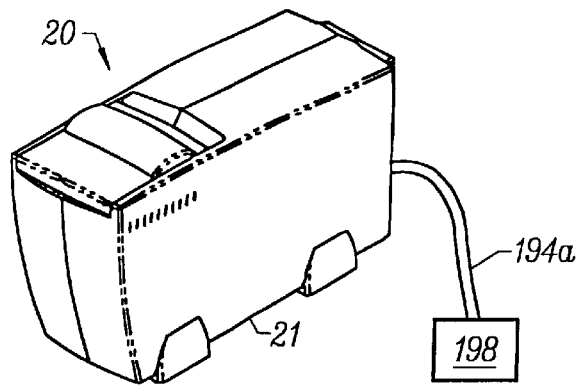
FIGS. 1A and 1B are a perspective view and an exploded perspective view, respectively, of an assembly of a microfluidic controller and detector system in accordance with the present invention.
Figure 1B:
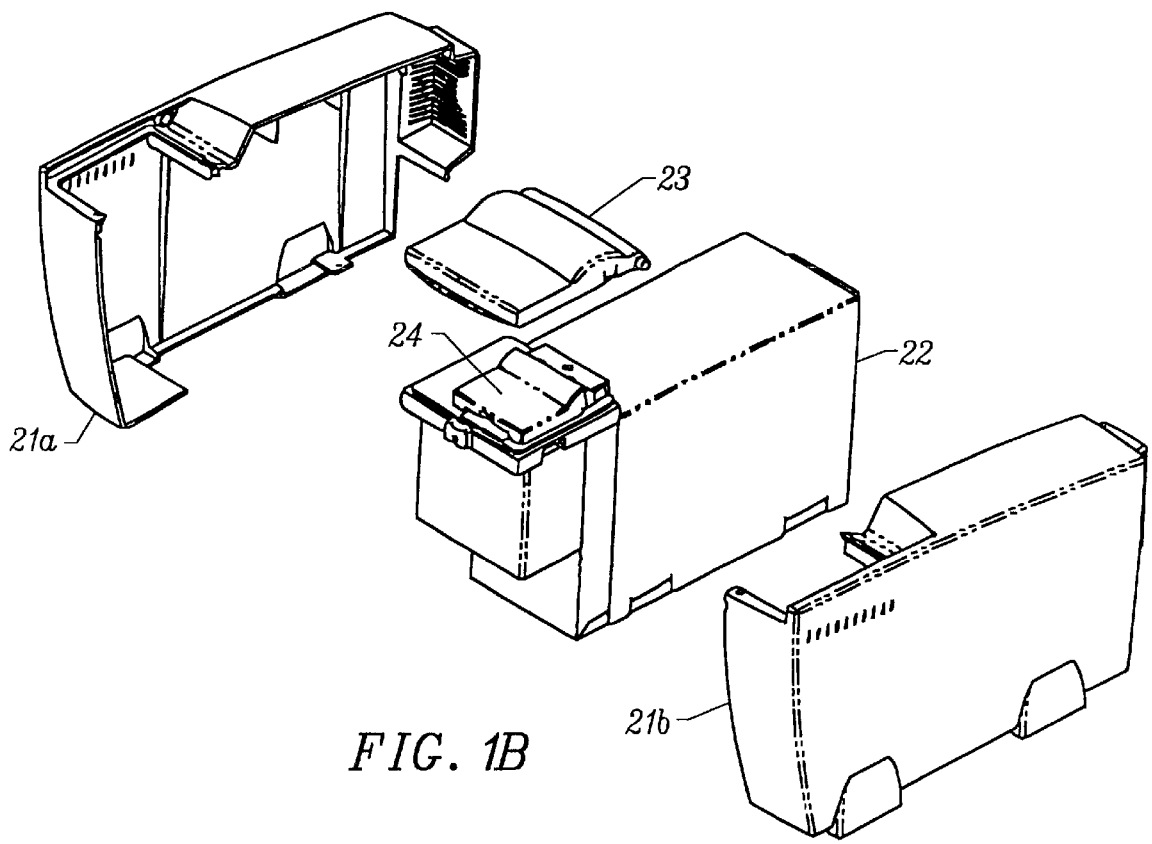

FIGS. 1A and 1B are a perspective view and an exploded perspective view, respectively, of an assembly of a microfluidic controller and detector system 20. Microfluidic controller and detector system 20 includes a housing 21, preferably including a first portion 21a and a second portion 21b. Housing 21 generally encloses a main unit 22. A lid 23 is optionally rotatively coupled to housing 21 for covering a clamshell unit 24 supported by main unit 22.

Figure 2A:
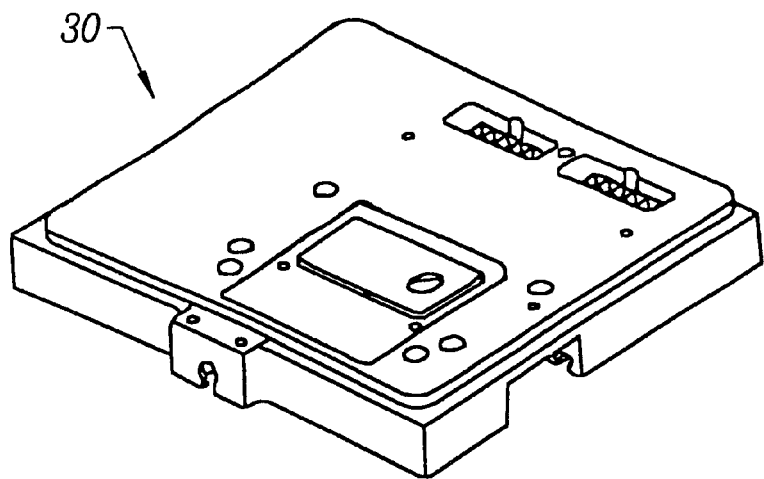
FIGS. 2A and 2B are a perspective view and an exploded perspective view, respectively, of a base plate assembly for a clam shell unit of the controller and detector system of FIGS. 1A and 1B.
Figure 2B:
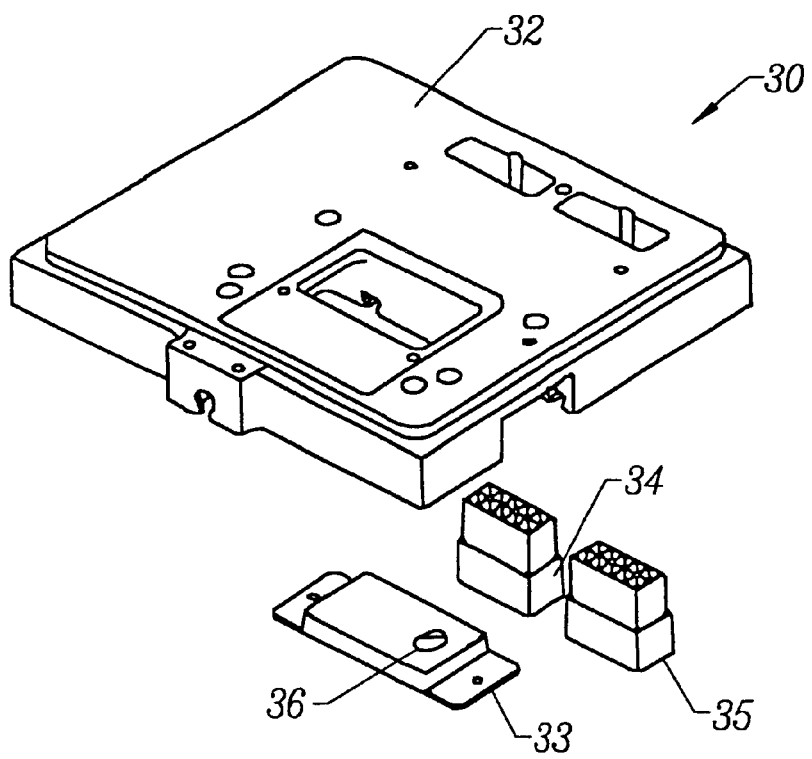

FIGS. 2A and 2B are a perspective view and an exploded perspective view, respectively, of a base plate assembly 30 for clam shell unit 24 of controller and detector system 20. As shown, clamshell unit 24 preferably includes a base plate assembly 30. Base plate assembly 30 generally includes a base plate 32, a heat sink 33 and two connector plugs 34, 35. As shown, heat sink 33 includes a bore 36 defined therein.

Figure 3A:
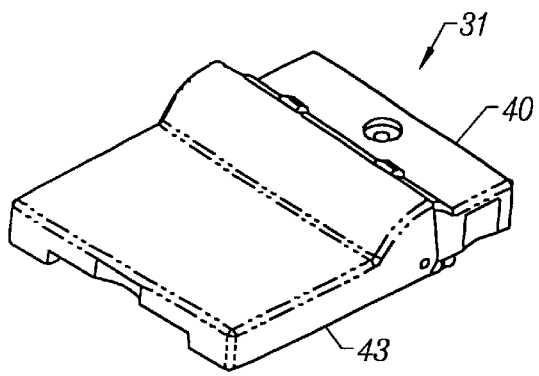
FIGS. 3A, 3B, and 3C are a top perspective view, a bottom perspective view, and an exploded bottom perspective view, respectively, of an electrode assembly for the clam shell unit of the controller and detector system of FIGS. 1A and 1B.
Figure 3B:
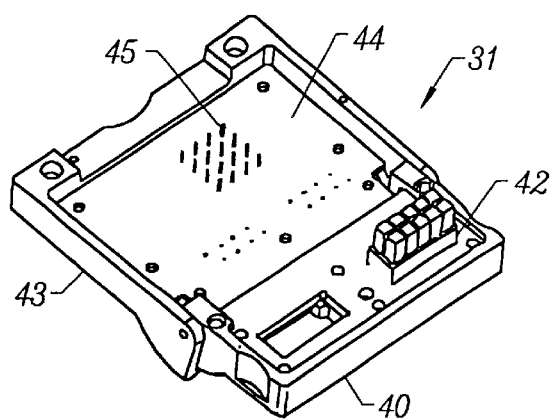
Figure 3C:
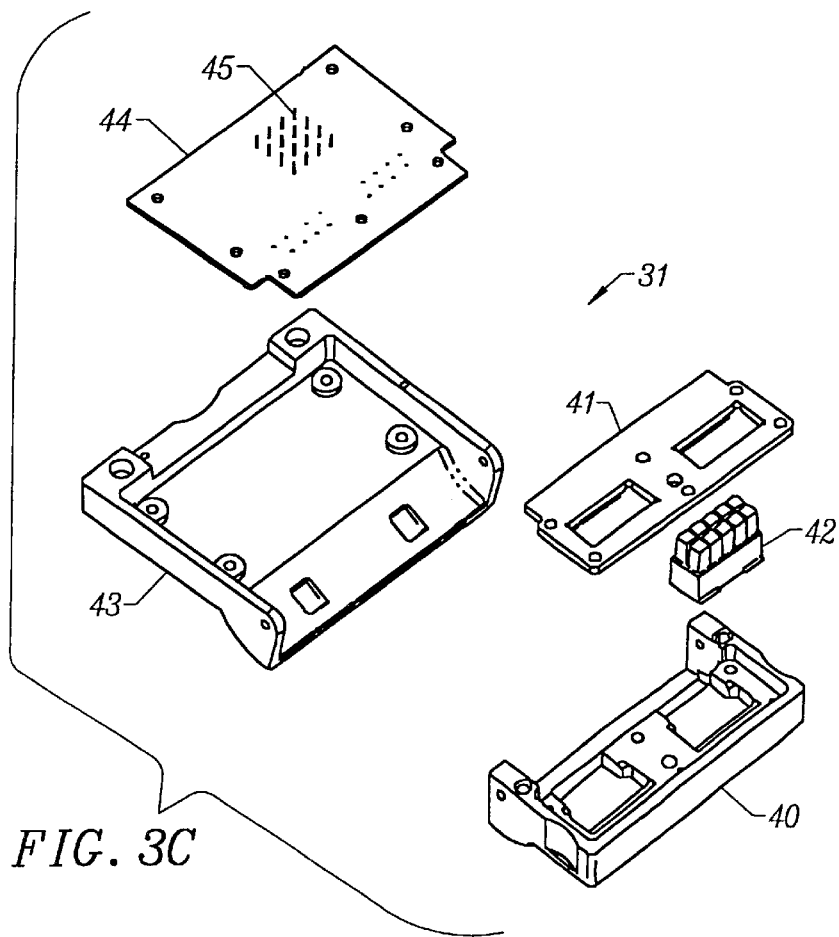

FIGS. 3A, 3B, and 3C are a top perspective view, a bottom perspective view, and an exploded bottom perspective view, respectively, of an electrode assembly 31 of the clam shell unit 24 of the controller and detector system 20. As shown, clamshell unit 24 referably includes an electrode assembly 31. Electrode assembly 31 typically includes a connector unit 40 that includes a connector plate 41 and a connector receptacle 42. The connector plate 41 is coupled to connector unit 40 in any suitable manner and holds connector receptacle 42 in place therein.

Electrode assembly 31 of the clamshell unit 24 optionally further includes a lid 43 rotatively coupled to detector connector unit 40 in any suitable manner. An electrode printed circuit board ("PCB") 44 having a plurality of electrodes 45 is typically disposed in lid 43. Electrode PCB 44 can be coupled to lid 43 in any suitable manner. Optionally, PCB 44 comprises a plate of hydrophobic material, such as KEL-F™, PCTFE, TEFLON™, polypropylene, polyethylene, on a side of PCB 44 shown in FIG. 3B which interfaces with the fluidic device such that electrodes 45 can be inserted therethrough. Electrodes 45 preferably extend to an opposing side of PCB 44 for connection to electrical leads (not shown). The plate of hydrophobic material, e.g., KEL-F™, PCTFE, TEFLON™, polypropylene, polyethylene, advantageously resists or reduces formation of condensation which could lead to electrical shorting.

Figure 3D:
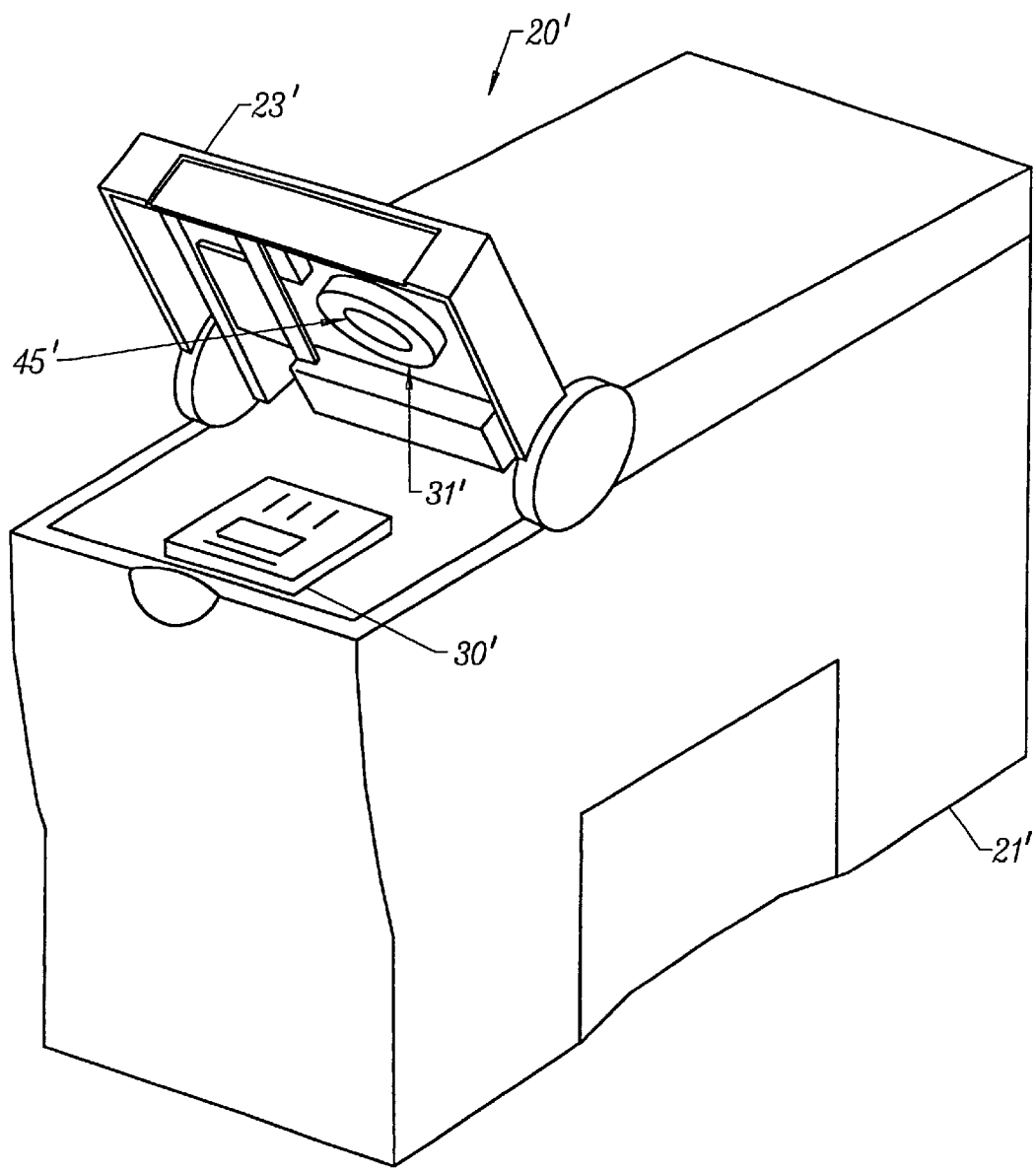
FIG. 3D is a perspective view of another assembly of a microfluidic controller and detector system in accordance with the present invention.

FIG. 3D is a perspective view of an alternative assembly of a microfluidic controller and detector system 20'. The microfluidic controller and detector system 20' is similar to the microfluidic controller and detector system 20 described above. For purposes of clarity, only key differences between system 20' and system 20 are noted below.

As shown, the microfluidic controller and detector system 20' includes a housing 21' and a lid 23' rotatively coupled to the housing 21' for covering a clamshell unit 24'. The clamshell unit 24' typically includes a base plate assembly 30' and an electrode assembly 31'. As shown, the clamshell unit 24' does not include a lid, but rather, the electrode assembly 31' of the clamshell unit 24' is disposed on an interior side of the lid 23' of the housing 21'. The electrode assembly 31' includes a plurality of electrodes 45' disposed therein for interfacing with a fluidic device, such as a microfluidic chip. In addition, the clamshell unit 24' of the microfluidic controller and detector system 20' provides a replaceable personality cassette. The electrode assembly 31', or the personality cassette, is replaceable and is easily removed from the lid 23' of the housing 21' such that it does not require detaching the clamshell lid from the clamshell unit, as is typically the case with the above-described microfluidic controller and detector system 20 embodiment. For example, a given electrode assembly 31' can be replaced with a differently configured electrode assembly 31', if necessary, for a different type of chip. The electrode assembly 31' is typically slidable into a track on the lid 23' of the housing 21'.

Figure 4A:
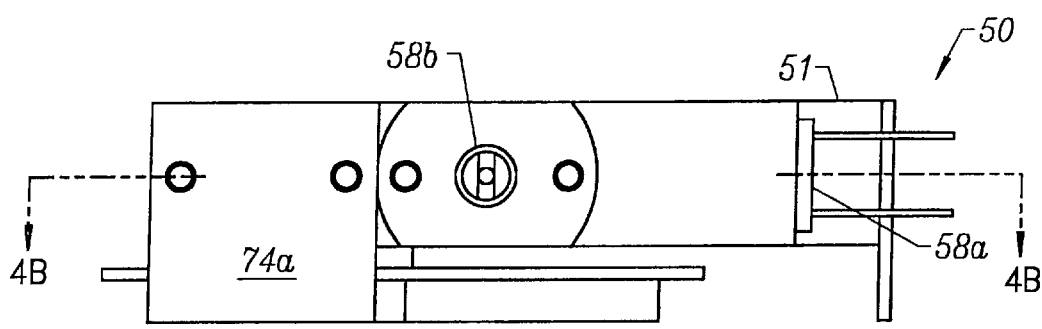
FIGS. 4A, 4B, and 4C are a bottom view, a side cross-sectional view taken at line 4B—4B in FIG. 4A, and an exploded perspective view, respectively, of an optic block assembly for the microfluidic controller and detector system of FIGS. 1A and 1B.
Figure 4B:
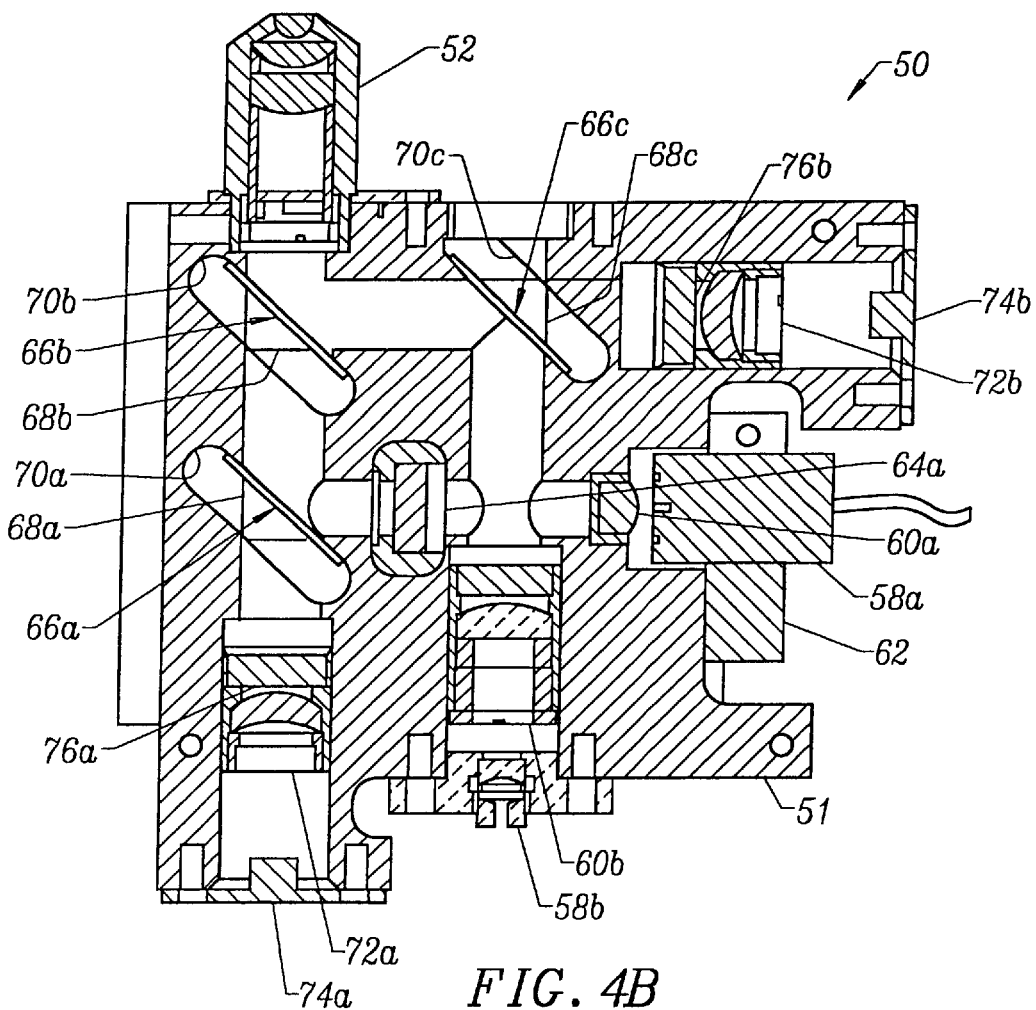
Figure 4C:
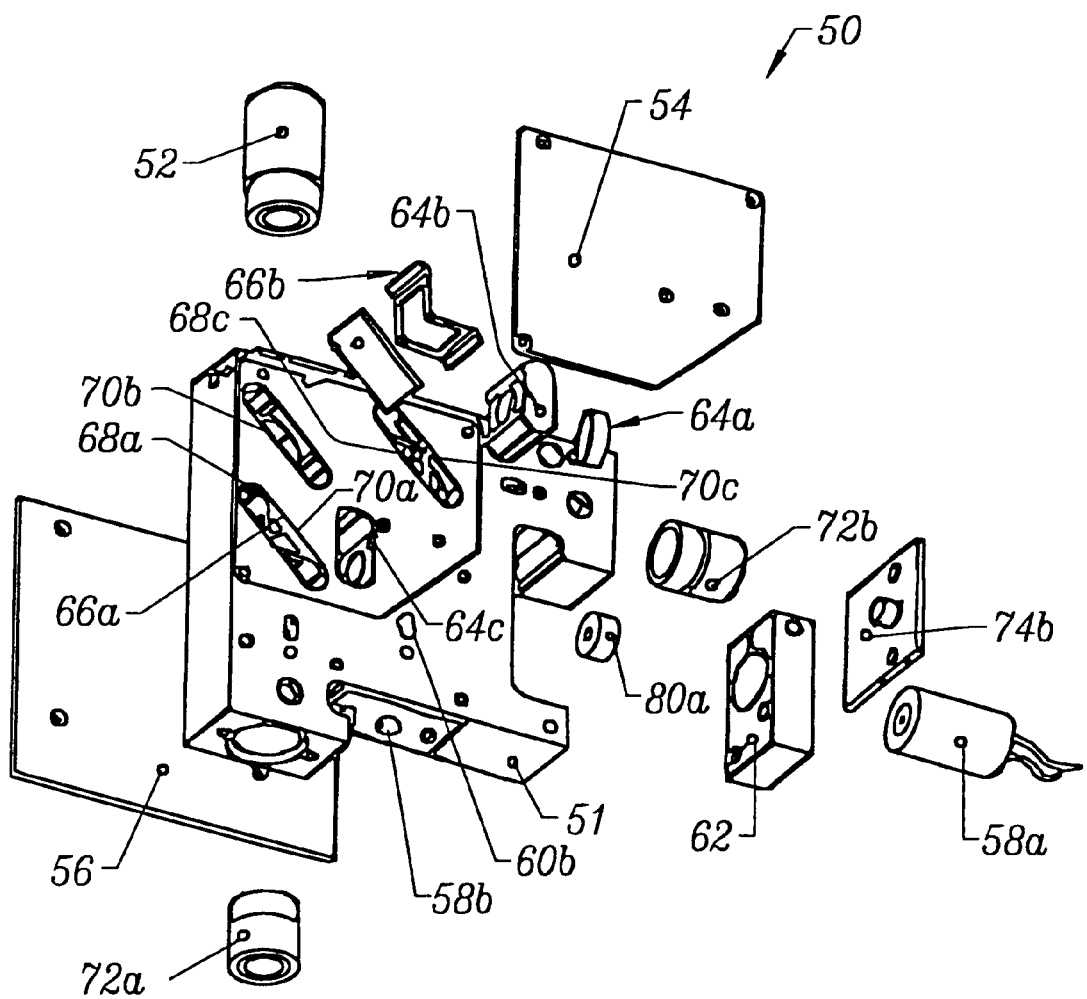
Figure 4C:
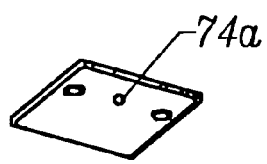
Figures 1, 4D:
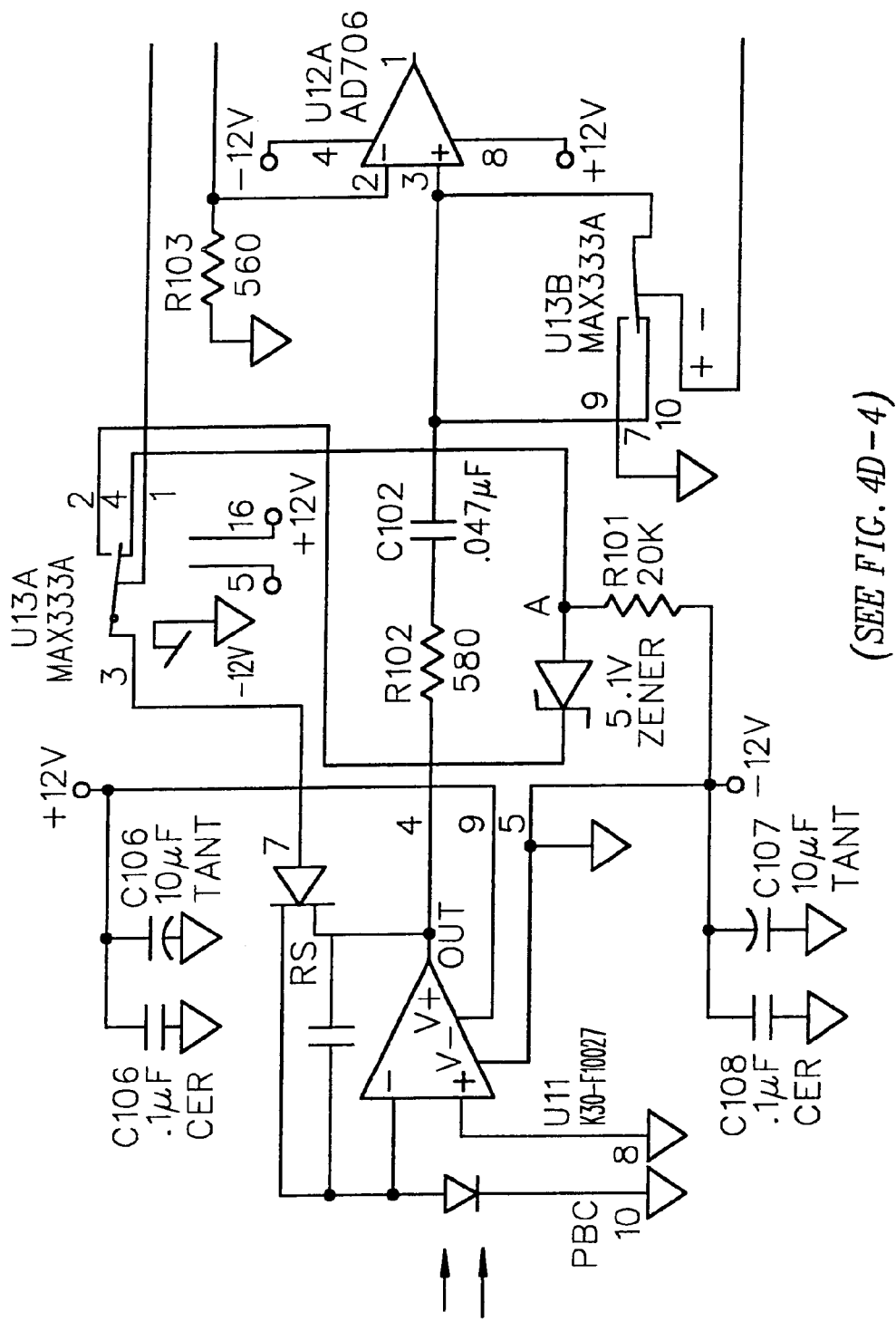
FIG. 4D is a schematic of an optics detector circuit.

FIGS. 4A, 4B, and 4C are a bottom view, a side cross-sectional view taken at line 4B—4B in FIG. 4A, and an exploded perspective view, respectively, of an optic block assembly 50 for microfluidic controller and detector system 20. Optic block assembly 50 is preferably disposed within the main unit and under the clamshell unit. Optic block assembly 50 generally comprises an optic block housing 51 in which an objective 52 is disposed. Optic block housing 51 is typically enclosed on one side by a cover plate 54 and on another side by an optic PCB 56. FIG. 4D is a schematic of one embodiment of the optics PCB 56.

Optic block assembly 50 preferably comprises one or more light sources, e.g., a first and a second light source 58a, 58b. The light sources can optionally be any number of light sources that provide the appropriate wavelength of light, including lasers, laser diodes, light emitting diodes (LED), and the like. As shown, first light source 58a is mounted within optic block housing 51 via a light source or laser mount 62. Light from first light source 58a is typically focused by a first lens tube assembly 60a. At least a portion of the light passing through laser lens tube assembly 60a then passes through a band pass filter 64a mounted to a laser lens holder 64b and disposed within an opening 64c defined by optic block housing 51. A first dichroic mirror 66a is preferably axially mounted by a mirror spring 68a at a 45 degree angle of incidence relative to the incoming light from first light source 58a. Dichroic mirror 66a and mirror spring 68a are preferably disposed within an opening 70a defined by optic block housing 51. Dichroic mirror 66a filters light by passing certain wavelengths while reflecting other wavelengths. For example, first dichroic mirror 66a typically filters the light emitted from light source 58a by reflecting only light with a wavelength less than approximately 670 nm. A portion of the light reflected by dichroic mirror 66a then passes through a second dichroic mirror 66b to objective 52. Second dichroic mirror 66b is mounted to a mirror spring 68b within an opening 70b defined by optic block housing 51. Second dichroic mirror 66b typically, for example, filters the light emitted from light source 58a by permitting only light with a wavelength above approximately 585 nm to pass therethrough.

The light from first light source 58a that passes through second dichroic mirror 66b is focused by objective 52 and impinges on, for example, a sample within microfluidic system 20. Fluorescence is typically emitted from the sample back through objective 52. Fluorescence at certain wavelengths is permitted to pass through second dichroic mirror 66b, through first dichroic mirror 66a, and is then focused by lens tube assembly 72a towards a first light detector PCB 74a.

Light from second light source 58b is generally focused by a second lens tube assembly 60b. A third dichroic mirror 66c is preferably axially mounted by a mirror spring 68c at a 45 degree angle of incidence relative to the incoming light from lens tube assembly 60b. Dichroic mirror 66c and mirror spring 68c are preferably disposed within an opening 70c defined by optic block housing 51. Third dichroic mirror 66c can, for example, further filter the light emitted from light source 58b by reflecting only light with a wavelength less than approximately 505 nm. At least a portion of the light reflected by third dichroic mirror 66c is then reflected by second dichroic mirror 66b to objective 52. Second dichroic mirror 66b can, for example, filter the light emitted from light source 58a by reflecting light with a wavelength less than approximately 585 nm.

The light from second light source 58b reflected by second dichroic mirror 66b is focused by objective 52 and impinges on, for example, a sample within microfluidic system 20. Fluorescence is typically emitted from the sample back through objective 52. Fluorescence at certain wavelengths is reflected by second dichroic mirror 66b and is permitted to pass through third dichroic mirror 66c. The fluorescence passing through third dichroic mirror 66c is then focused by lens tube assembly 72b towards a second light detector PCB 74b.

Each of lens tube assemblies 72a, 72b preferably includes a detection filter which filters the signal emitted from the sample. Detection filters clean up light emitted from the sample by removing scattered light such that light from the fluorescence light signal pass through while light from light source is filtered out. Lens tube assemblies 72a, 72b are positioned adjacent to light detector PCB 74a, 74b, respectively.

Each of light detectors 74a, 74b converts incoming light into electric signals. Detection system 20 is preferably coupled to the host computer 198 (shown in FIG. 1A) via a serial connection for transmitting detected light data to the computer for analysis, storage, and data manipulation. Light detectors 74a, 74b is optionally a photodiode, avalanche photodiode, photomultiplier tube, diode array, or imaging systems, such as charged coupled devices (CCDs), and the like. Light detectors 74a, 74b optionally includes, for example, an integrator and an analog-to-digital converter having an analog input coupled to an output of the integrator, as described in U.S. patent application Ser. No. 09/104,813, filed Jun. 25, 1998 which is incorporated herein by reference in its entirety.

In one preferred embodiment, first light source 58a comprises a red laser or a red laser diode. The red laser or red laser diode facilitates detection of fluorescent species that excite in the red range. Second light source 58b preferably comprises a blue light emitting diode ("LED") which can be used for multi-wavelength detection schemes and/or in less sensitive analyses, for example. First light detector 74a is preferably a photo diode where the lens tube assembly 72a includes a filter 76a for passing 682 nm centered wavelength with a bandwidth of approximately 20 nm. Second light detector 74b is preferably a photo diode where the lens tube assembly 72b includes a filter 76b for passing 525 nm with a bandwidth of approximately 20 nm. As shown, the filters 76a, 76b are contained in the lens tube assemblies 72a, 72b.

Some aspects of some of the components and functionality of optic block assembly 50 is further described in co-pending U.S. Provisional Application No. 60/143399, entitled "Light Source Power Modulation for use in Chemical and Biochemical Analysis" and filed on Jul. 12, 1999, the entirety of which is incorporated by reference herein.

Although system 20 described above is described for use with a microfluidic device containing a sample with a fluorescent label, it is to be understood that the system may be used to detect other types of labels including light absorbing labels and radioactive labels, for example.

Figure 5A:
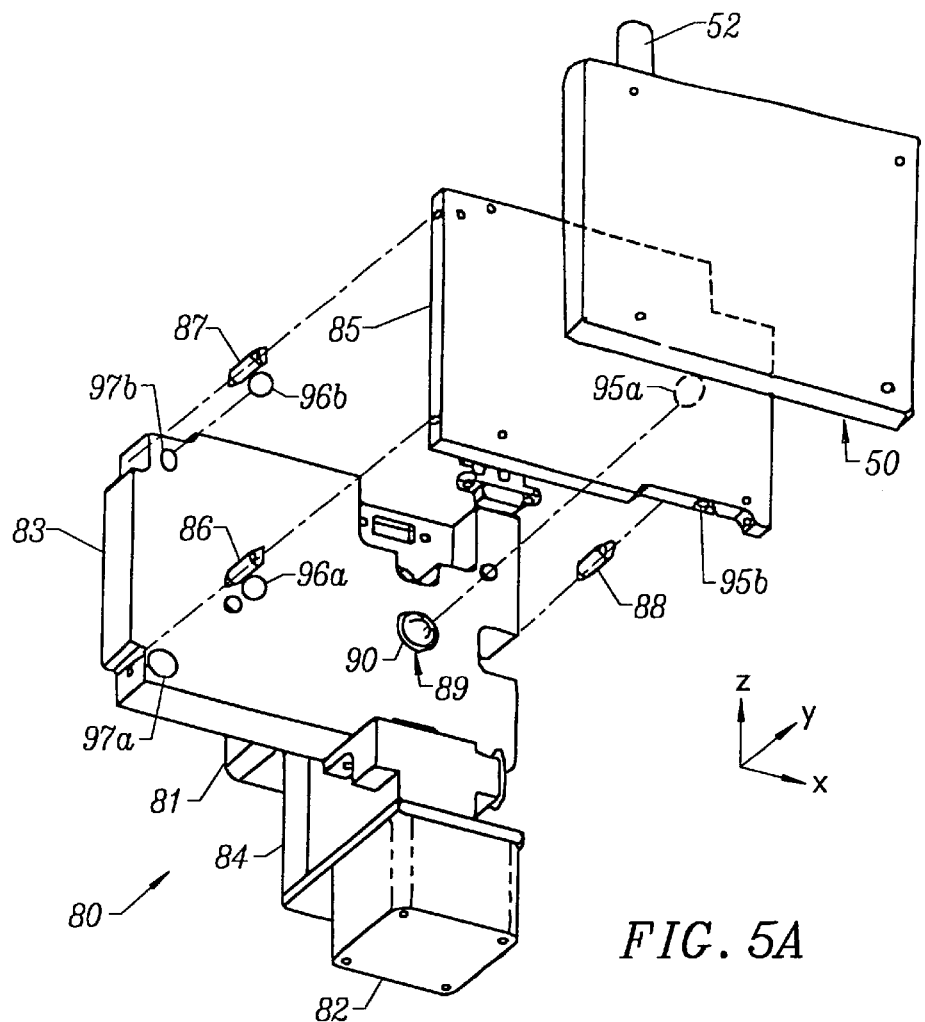
FIG. 5A is an exploded perspective view of a kinematic mounting assembly of the microfluidic controller and detector system illustrated in FIGS. 1A and 1B.

FIG. 5A is an exploded perspective view of a kinematic mounting assembly 80 of the microfluidic controller and detector system 20. Kinematic mounting assembly 80 is optionally coupled to optics block assembly 50 to align and focus the optics block relative to the analysis channel in the chip.

Kinematic mounting assembly 80 generally comprises a first and a second stepper motor 81, 82 mounted to a first plate 83 via an L bracket 84. First plate 83 is positioned adjacent a second plate 85 movable relative to first plate 83. First and second plates 83, 85 are movably coupled, such as by springs 86, 87, 88 coupled between the first and second plates with any suitable attachment mechanism such as set screws or pins (not shown). Three springs are preferred although one spring is generally centrally provided between first and second plates 83, 85.

Figure 5B:
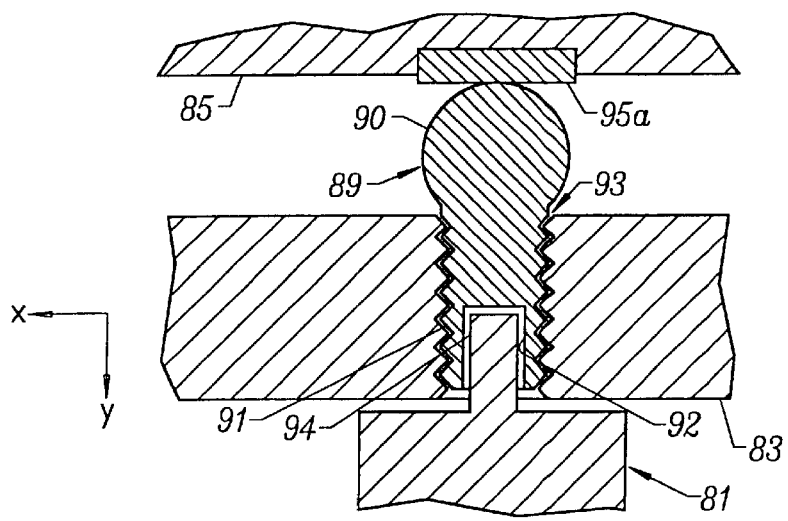
FIG. 5B is a simplified partial cross-section view of coupling of a stepper motor to plates of kinematic mounting assembly of FIG. 5A.

FIG. 5B is a simplified partial cross-section view of coupling of first stepper motor 81 to first and second plates 83, 85 of kinematic mounting assembly 80 via a first coupler 89. Coupler 89 comprises a ball shaped or rounded end 90, a threaded rod 91 extending from ball shaped end 90, and an internal opening 92 defined in rod 91. Threaded rod 91 is configured to engage with threads 93 of first plate 83 such that rod 91 is rotatable relative to first plate 83.

Internal opening 92 of rod 91 is optionally configured to slidably mate or slip fit with a shaft 94 of first stepper motor 81 such that rotation of the first stepper motor shaft result in rotation of coupler 89. For example, the internal rod opening and first stepper motor shaft have mating hexagonal cross-sectional shapes such that internal rod opening 92 defines a hex socket which shaft 94 of first stepper motor 81 serves as a mating hex key. Thus, as first stepper motor 81 rotates shaft 92, causing coupler 89 to rotate within first plate 83, coupler is translationally displaced in a Y direction to thereby increase or decrease a distance between first and second plates 83, 85. Alternatively, a flexible shaft coupling can be used.

Second plate 85 preferably provides a hard seat or surface 95a having approximately a diameter approximately same, one-half, one-fourth, or any suitable portion of a diameter of ball shaped end 90. Hard seat 95a generally comprises a material such as cubic zirconium such that wear from movement of ball shaped end 90 over hard seat 95a is minimized. Ball shaped end 90 preferably similarly comprises a hardened material such that its shape and size do not generally change over time due to wear.

Such an internally threaded bushing driven by a stepper motor with a ball or a ball shaped end riding on a seat is known in the art. Any other suitable coupling of the shaft of the stepper motor to the coupler can optionally be implemented. For example, a flexible elastomer shaft coupling utilizing a helical spring can be utilized as the coupler.

Although not shown, second stepper motor 82 optionally has a configuration similar to that of first stepper motor 81. For example, second stepper motor 82 includes a shaft configured to slidably engage or slip fit with an internal opening of a second coupler. Further, the internal rod opening and second stepper motor shaft optionally have mating hexagonal cross-sectional shapes such that the internal rod opening defines a hex socket to which the shaft of second stepper motor 82 serves as a mating hex key.

The second coupler generally comprise a ball shaped or rounded end, a threaded rod extending from the ball shaped end, and the internal opening to which the shaft of second stepper motor 82 is typically engaged. The threaded rod is optionally configured to engage with internal threads of a member or an extension stationary relative to and/or coupled to second stepper motor 82, first plate 83, and/or mounting bracket 84, for example. A spring is preferably provided along a Z direction to couple second stepper motor 82 to second plate 85. For example, the Z direction spring is typically coupled via a pin or a set screw to the member or extension on one end and to second plate 85 on another of the Z direction spring.

A side surface of second plate 85 preferably provides a hard seat or surface 95b having approximately a diameter approximately same, one-half, one-fourth, or any suitable portion of a diameter of the ball shaped end of the second coupler. Hard seat 95b is generally similar in construct as hard seat 95a and serves a similar purpose of minimizing wear from movement of the ball shaped end of the second coupler over hard seat 95b. The second coupler similarly generally comprises a hardened material such that its shape and size do not generally change over time due to wear.

The configuration of second stepper motor 82 is such that rotation of its shaft causes rotation of the second coupler within the internally threaded stationary member or extension. The second coupler is thus translationally displaced in a Z direction to thereby rotate second plate 85 relative to first plate 83 about a pivot.

Thread engagement between the couplers and first plate 83 effectively gears down the stepper motors to allow for accurate and precise relative positioning of first and second plates 83, 85. The resolution of such positioning is typically determined and selected based upon the threads and parameters of each stepper motor. Resolution of approximately 0.8 μm of displacement or travel for each step of the stepper motor can be easily achieved.

Kinematic mounting assembly 80 preferably provides a pivot about which second plate 85 is moved relative to first plate 83 in each of the Y and Z directions. In the embodiment shown in FIG. 5A, kinematic mounting assembly 80 provides two pivots, each comprising a ball 96a, 96b and a corresponding seat 97a, 97b, respectively. Seats 97a, 97b are optionally provided by first plate 83.

One of seats 97a, 97b is optionally a cone shaped recess configured to receive approximately one-half of a corresponding ball therein such that the corresponding ball can rotate within the recess. The ball and cone shaped recess combination generally serve as a pivot for movement of second plate 85 relative to first plate 83 such as in the Y direction with actuation of first stepper motor 81 and/or in the Z direction with actuation of second stepper motor 82. The other of seats 97a, 97b is optionally a hard surface seat similar to seat 95a (shown in FIG. 5B) such that a corresponding ball can slidably move in an X-Z plane. The ball and hard surface seat combination generally serves as a third contact point, in addition to contacts points provided by ball 90 of coupler 89 and the pivot comprising the cone shaped recess and the corresponding ball, to define a plane.

Each of balls 96a, 96b is typically attached by any suitable attachment mechanism to second plate 85. Alternatively, balls 96a, 96b are unattached to and disposed between first and second plates 83, 85 and are confined to between first and second plates 83, 85 via springs 86, 87, 88.

Preferably, first and second plates 83, 85 are coupled to the optic block assembly such that the first plate 83 is stationary relative to the base plate assembly 30 and the second plate 85 is coupled to the optic block housing. Alternatively, the second plate 85 are coupled to the objective such that the objective can be moved and positioned over a distance of up to approximately 3 mm, for example, to scan and locate channels or a detection window of a microfluidic chip as will be described below and/or such that the objective can be focused by displacing the objective in a Z direction, such as up to approximately 0.5 mm, relative to the detection window of the microfluidic chip.

In one preferred embodiment, each of balls 96a, 96b has a diameter of approximately 6 mm such that the pivot comprising the cone shaped recess and the corresponding ball provides a clearance between first and second plates 83, 85 of approximately 3 mm.

Figure 6A:
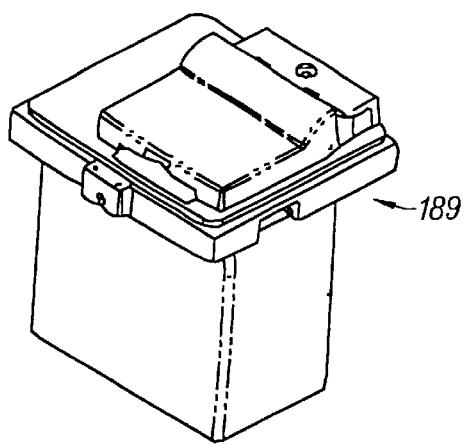
FIG. 6A is a perspective view of a reader assembly of the microfluidic controller and detector system illustrated in FIGS. 1A and 1B.
Figure 6B:
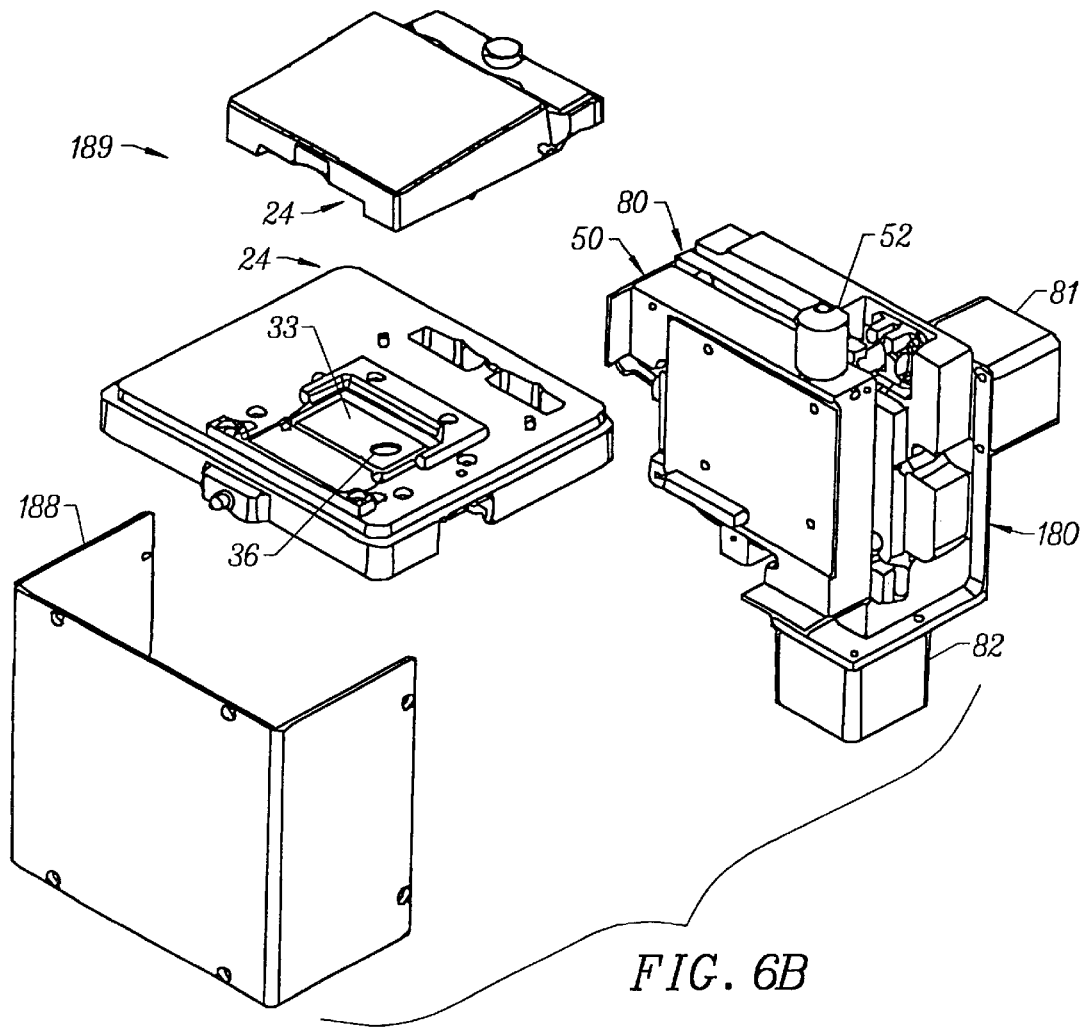
FIG. 6B is an exploded perspective view of the wiggler and reader assemblies of the microfluidic controller and detector system illustrated in FIGS. 1A and 1B.
Figure 6C:
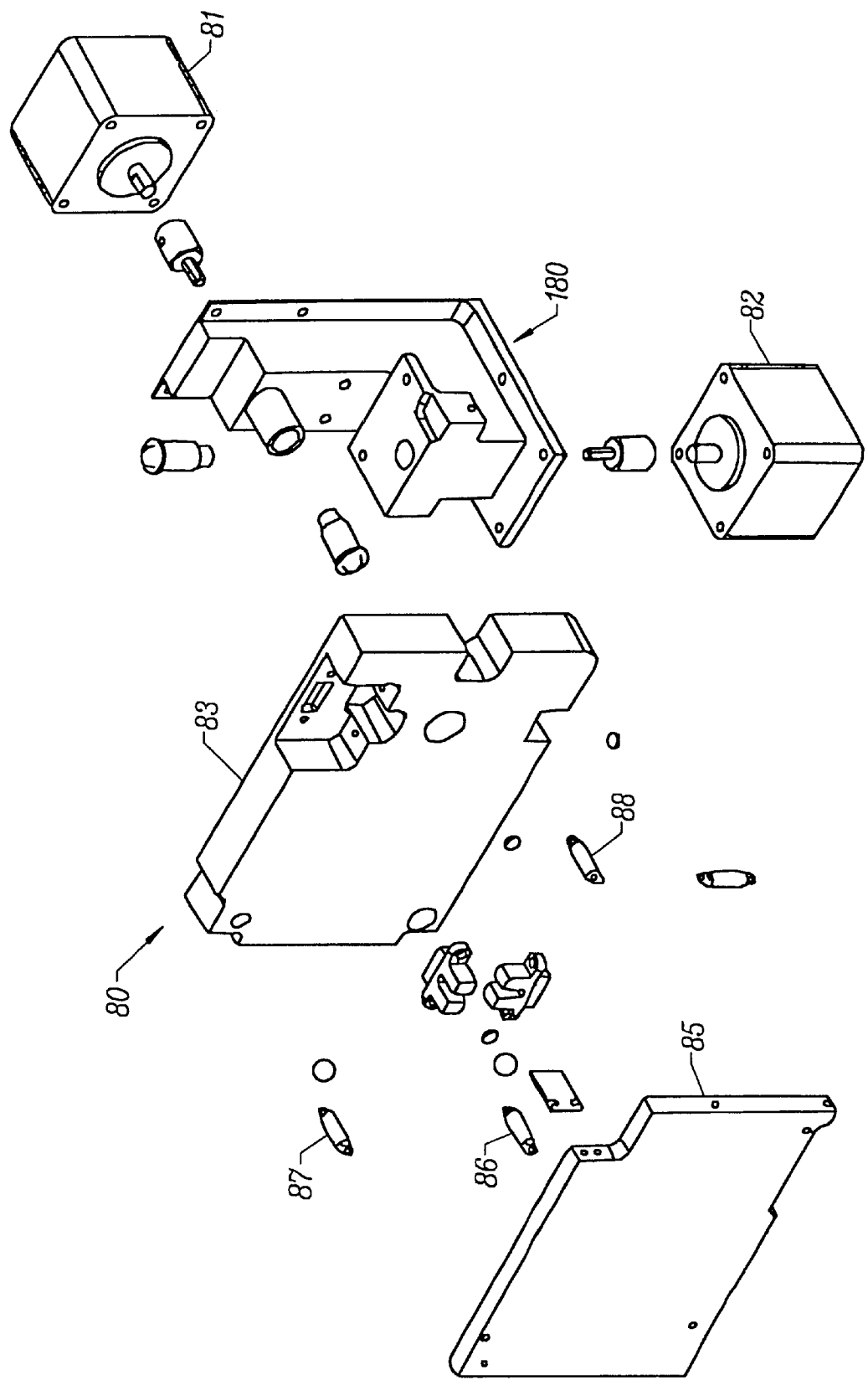
FIG. 6C is an exploded perspective view of the kinematic mounting assembly.
Figure 7:
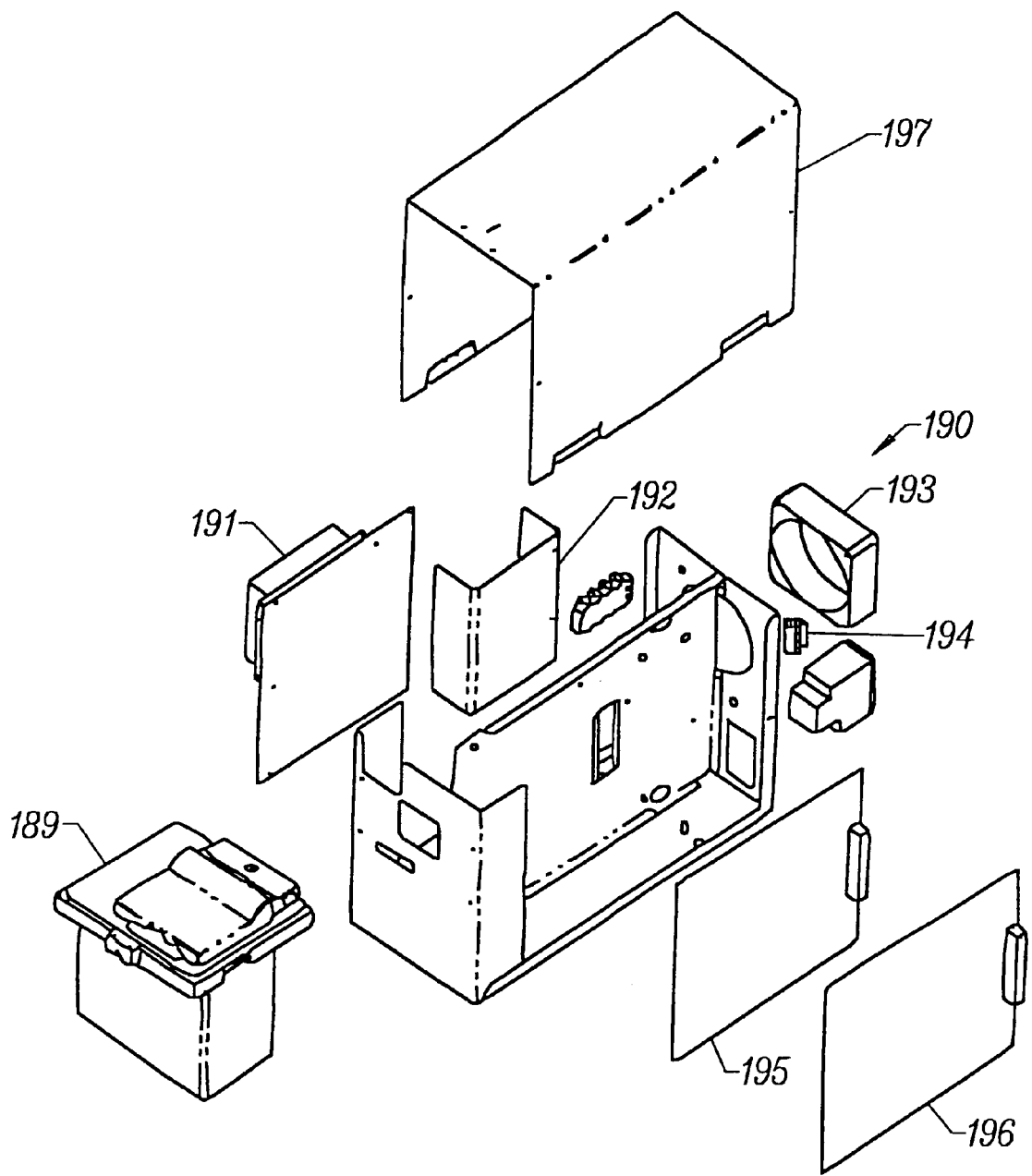
Figure 8:
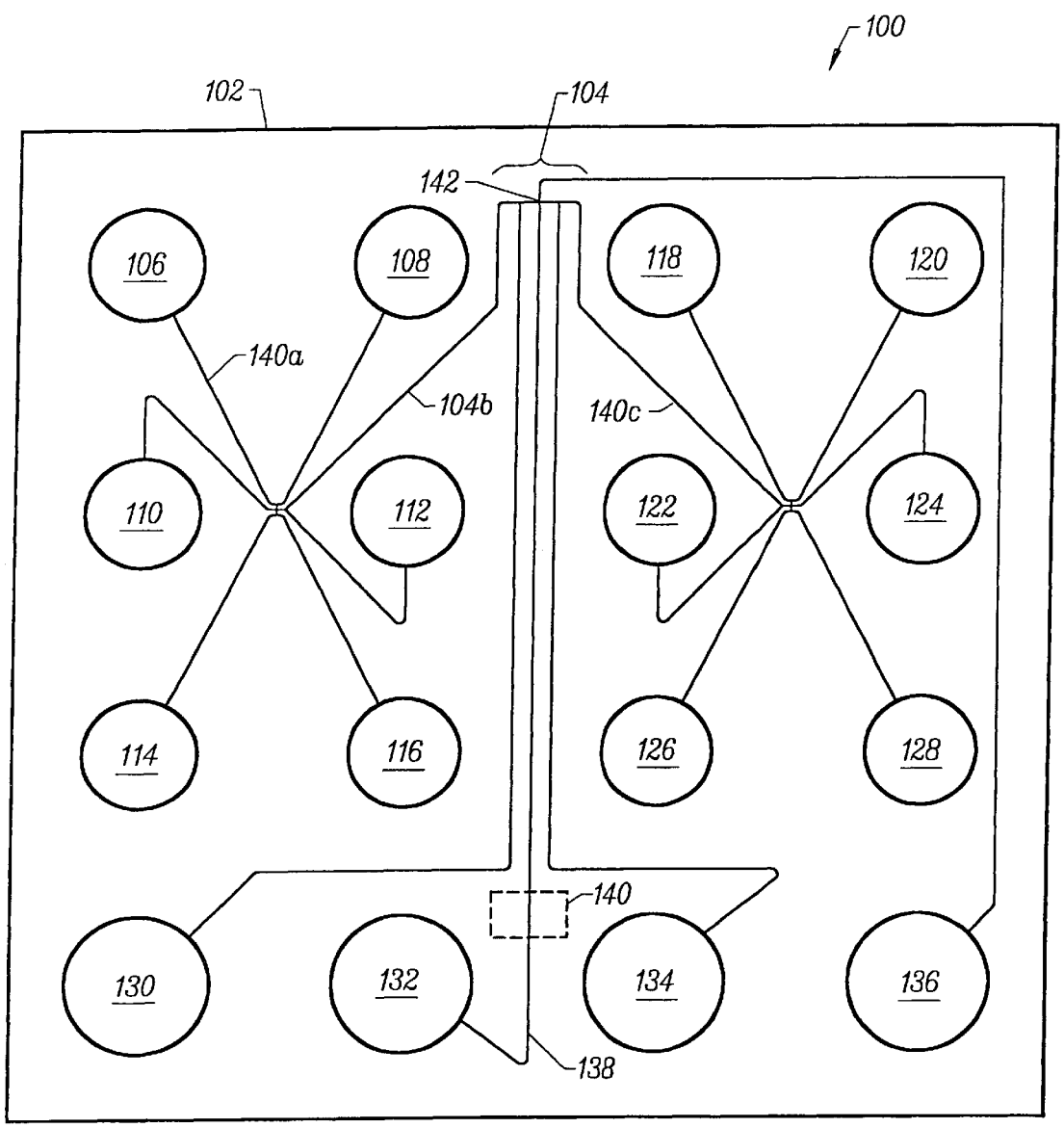
Figure 9A:
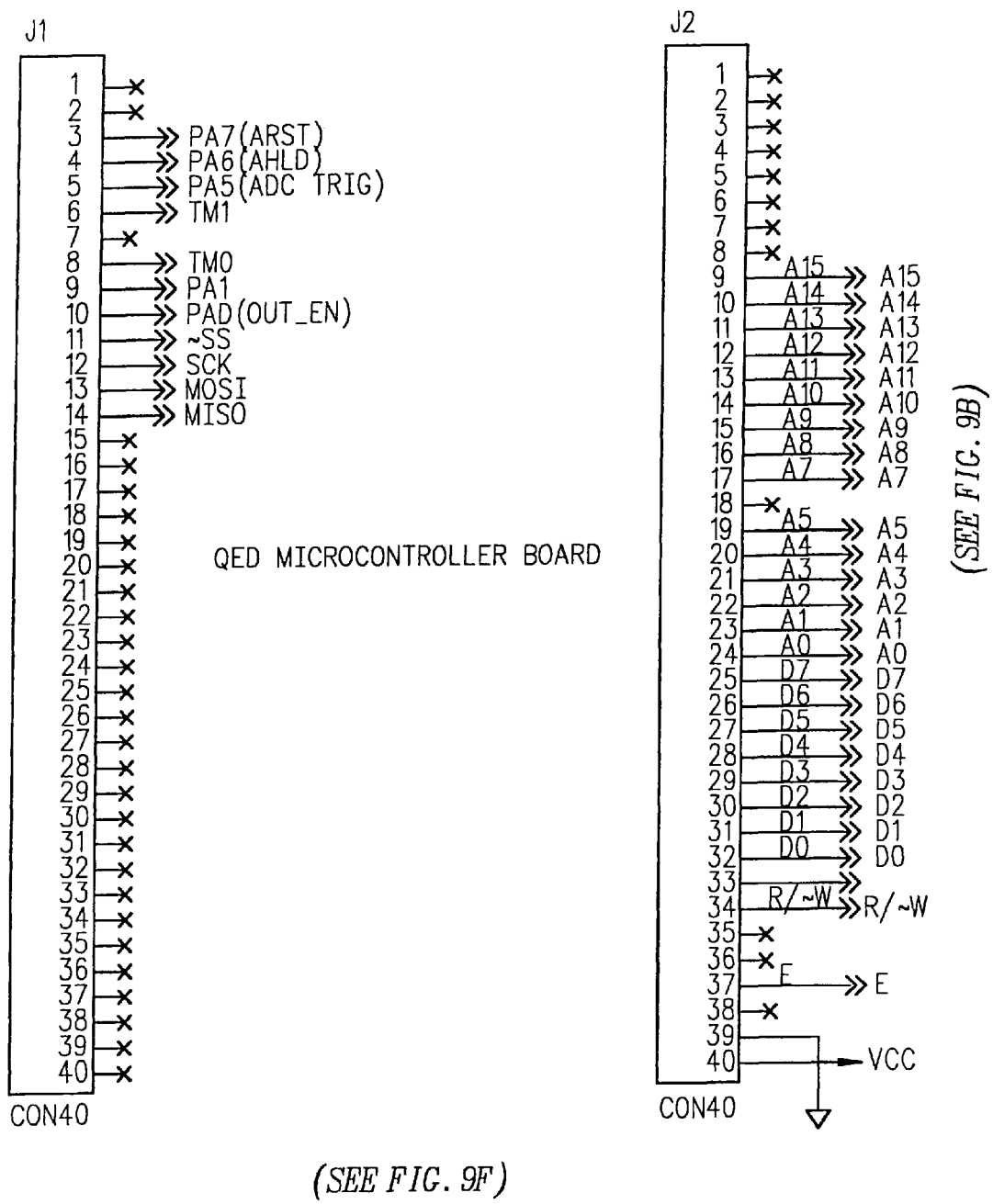
FIG. 9 is a schematic of an embodiment of a system control circuitry board.
Figure 9B:
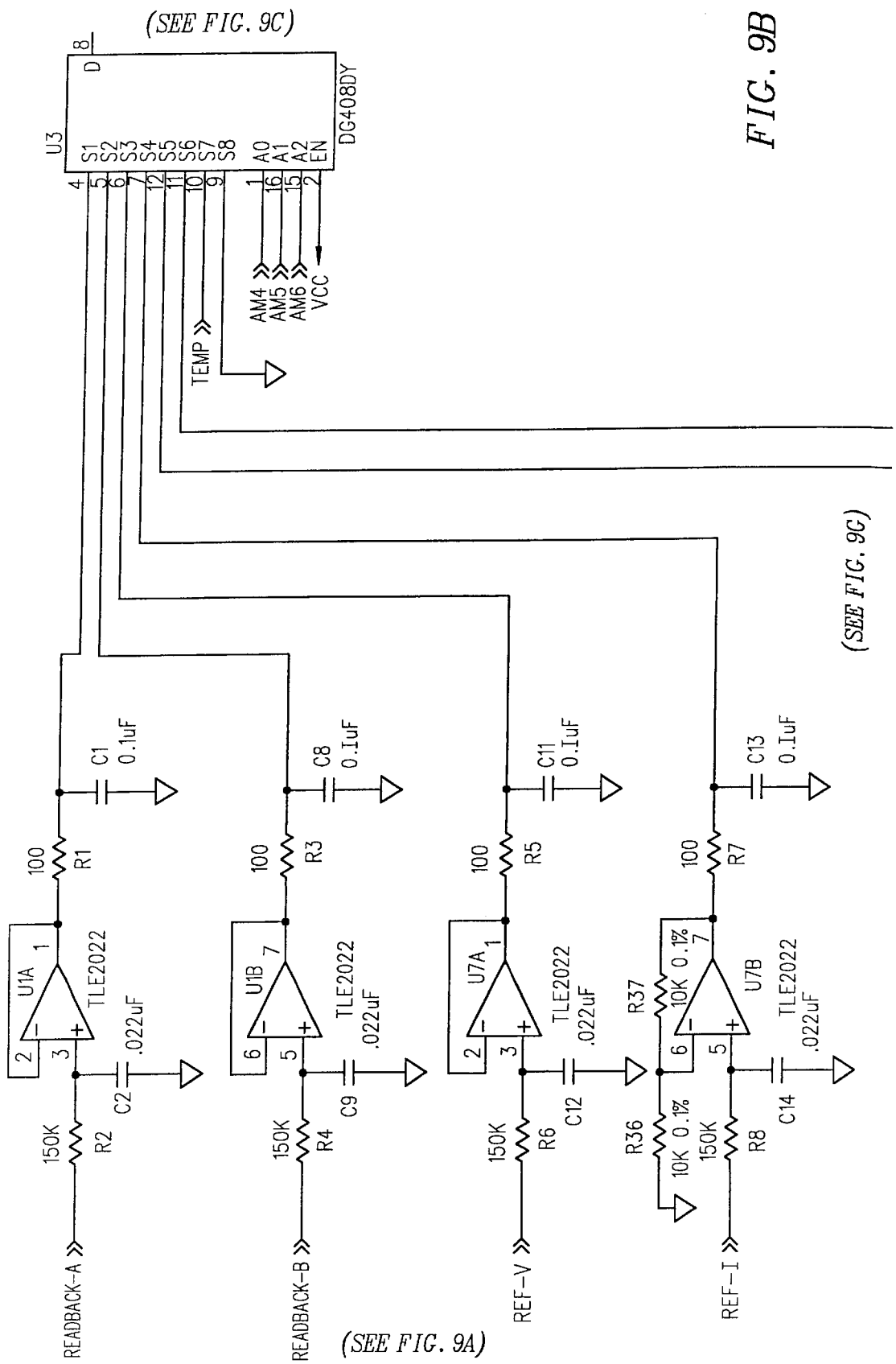
Figure 9C:
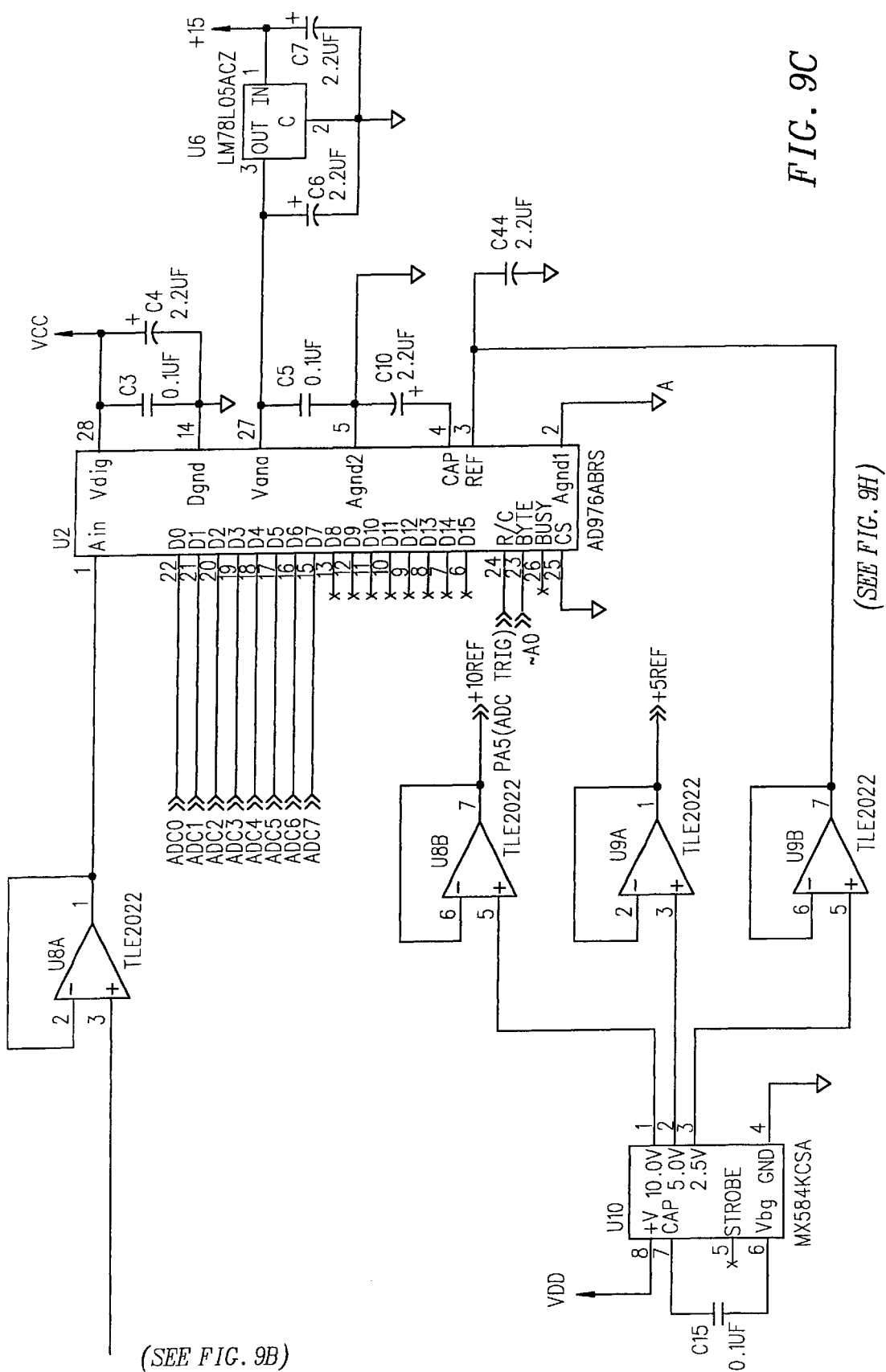
Figure 9D:
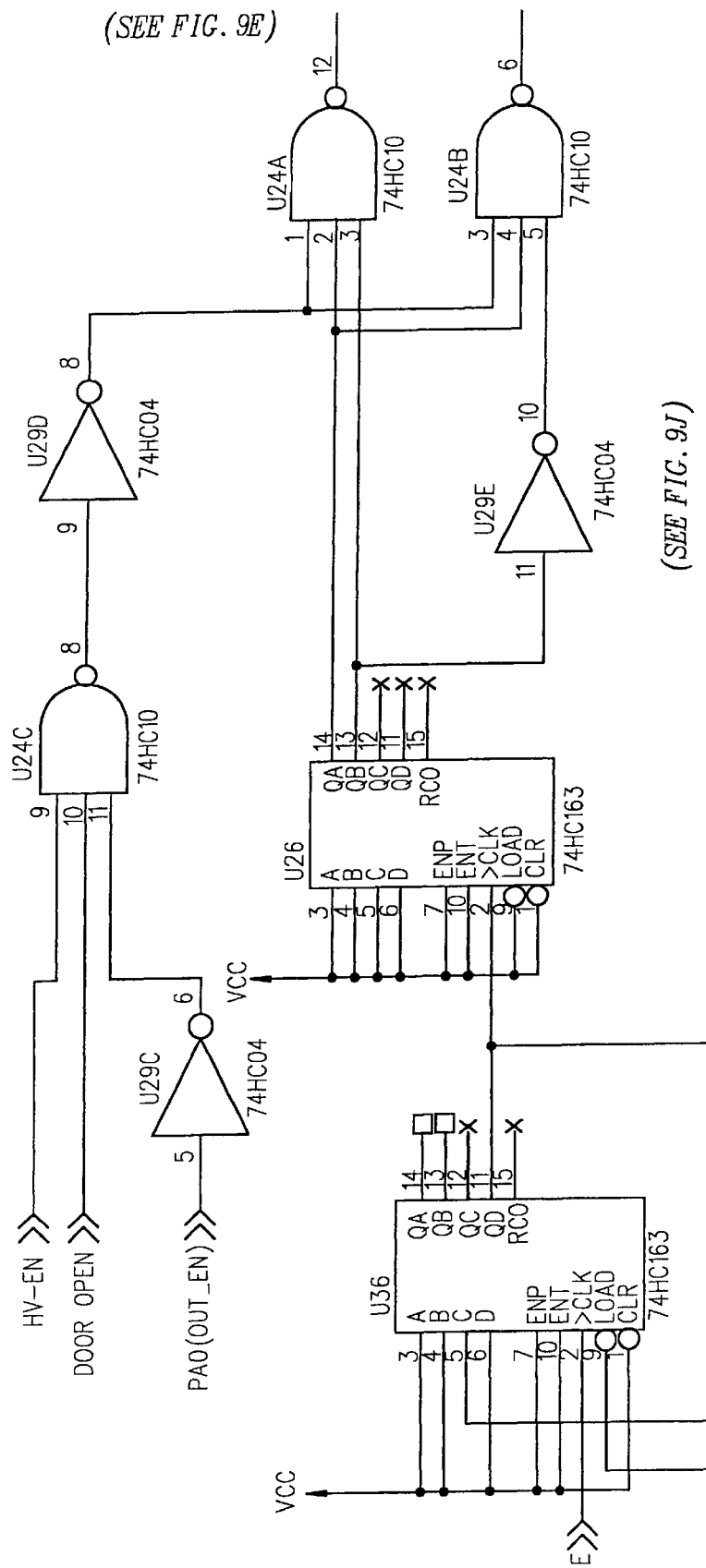
Figure 9E:
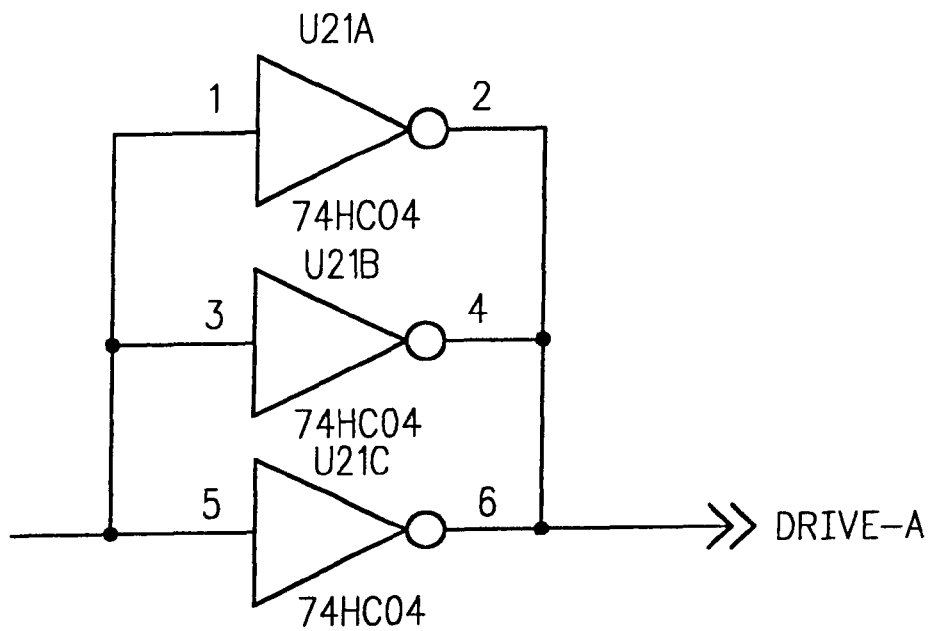
Figure 9E:
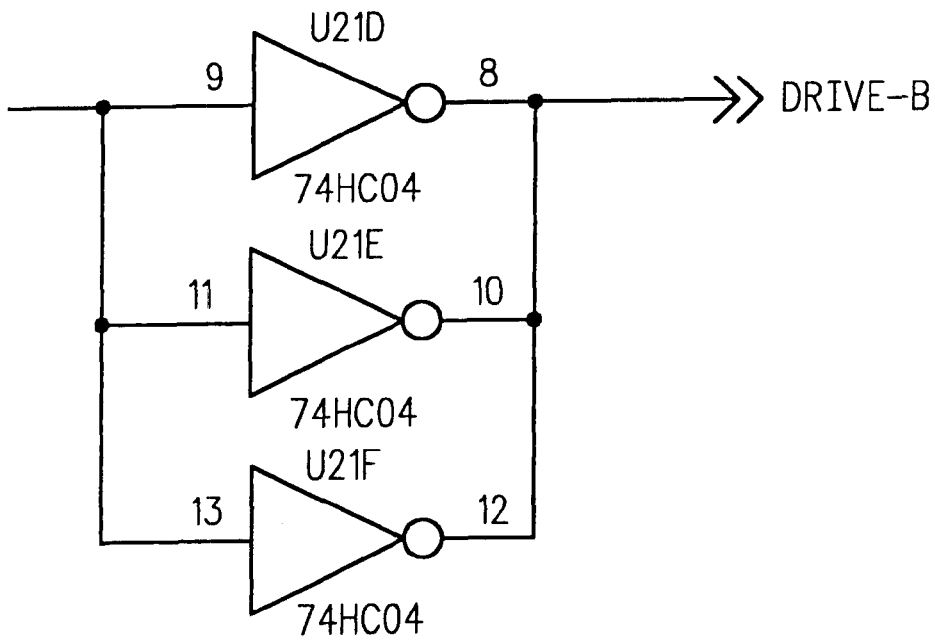
Figure 9F:
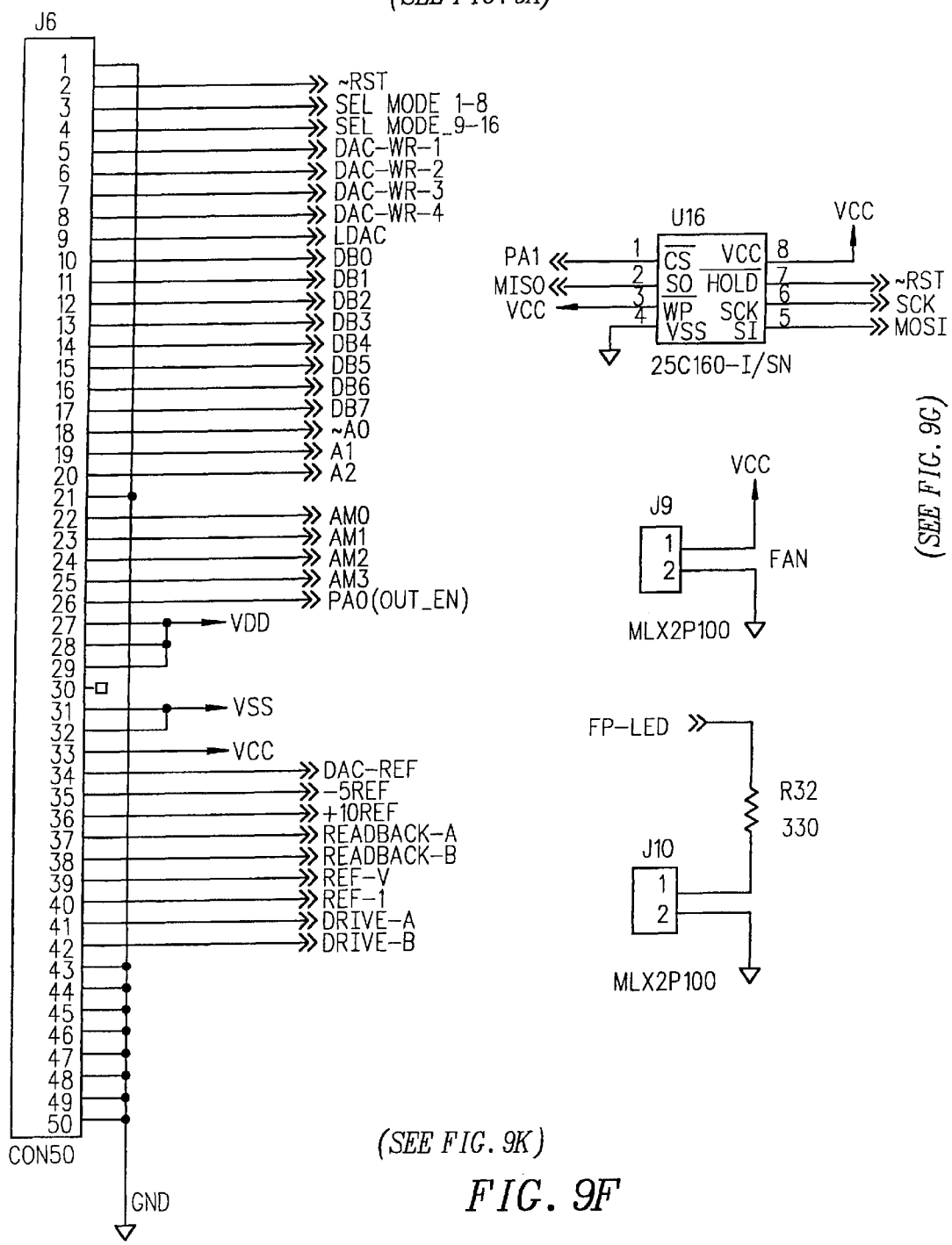
Figure 9H:
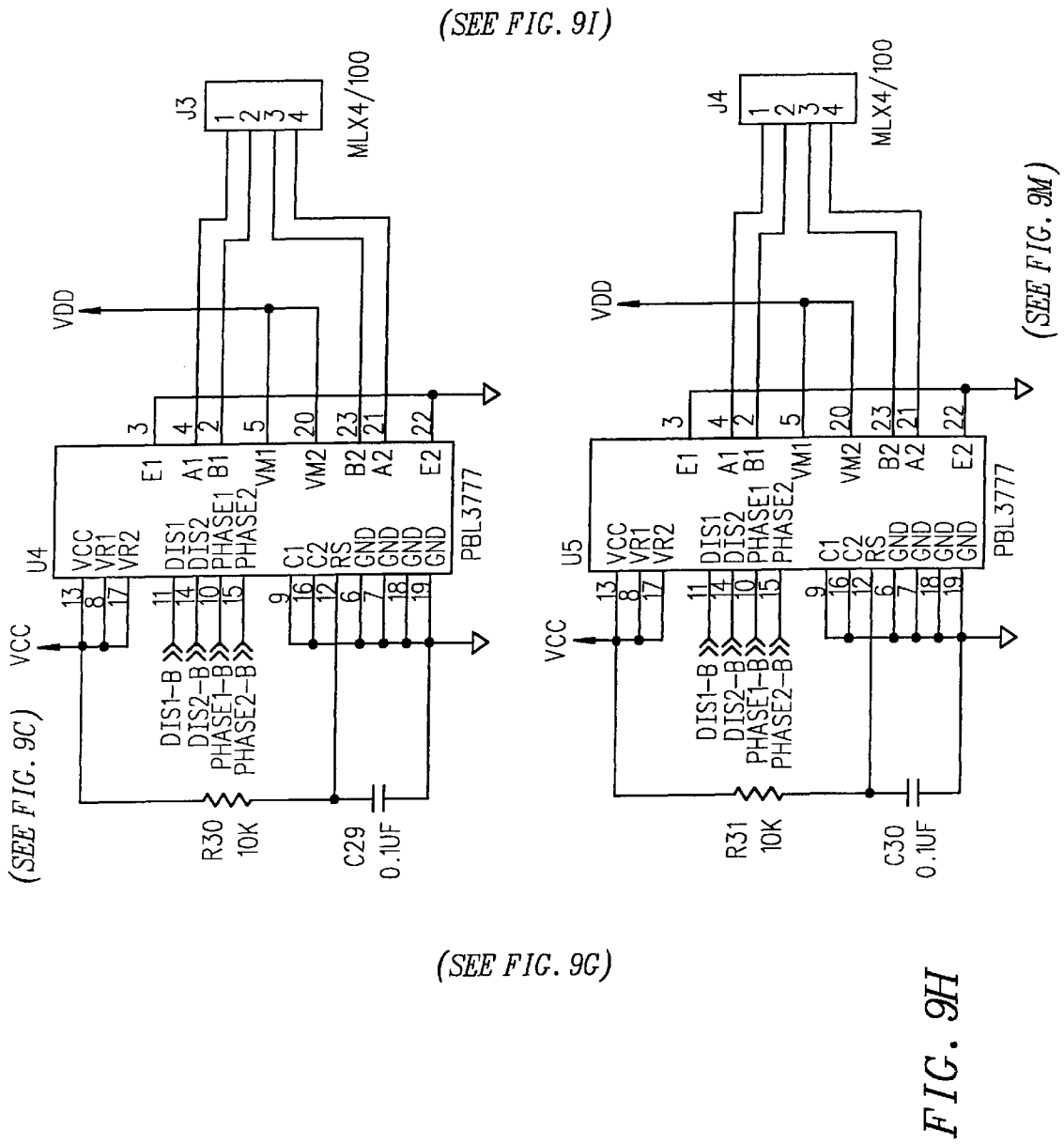
Figure 9I:
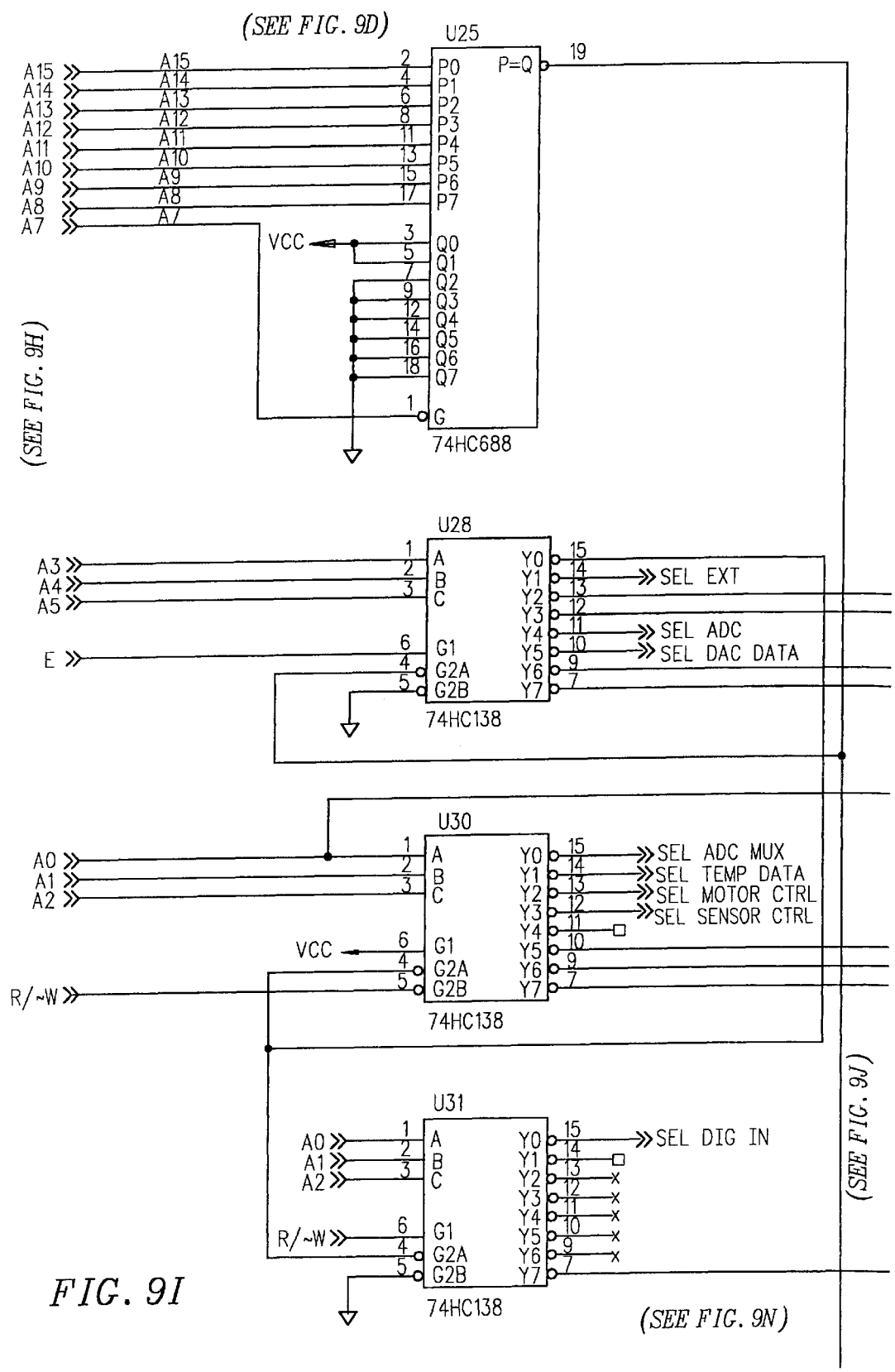
Figure 9J:
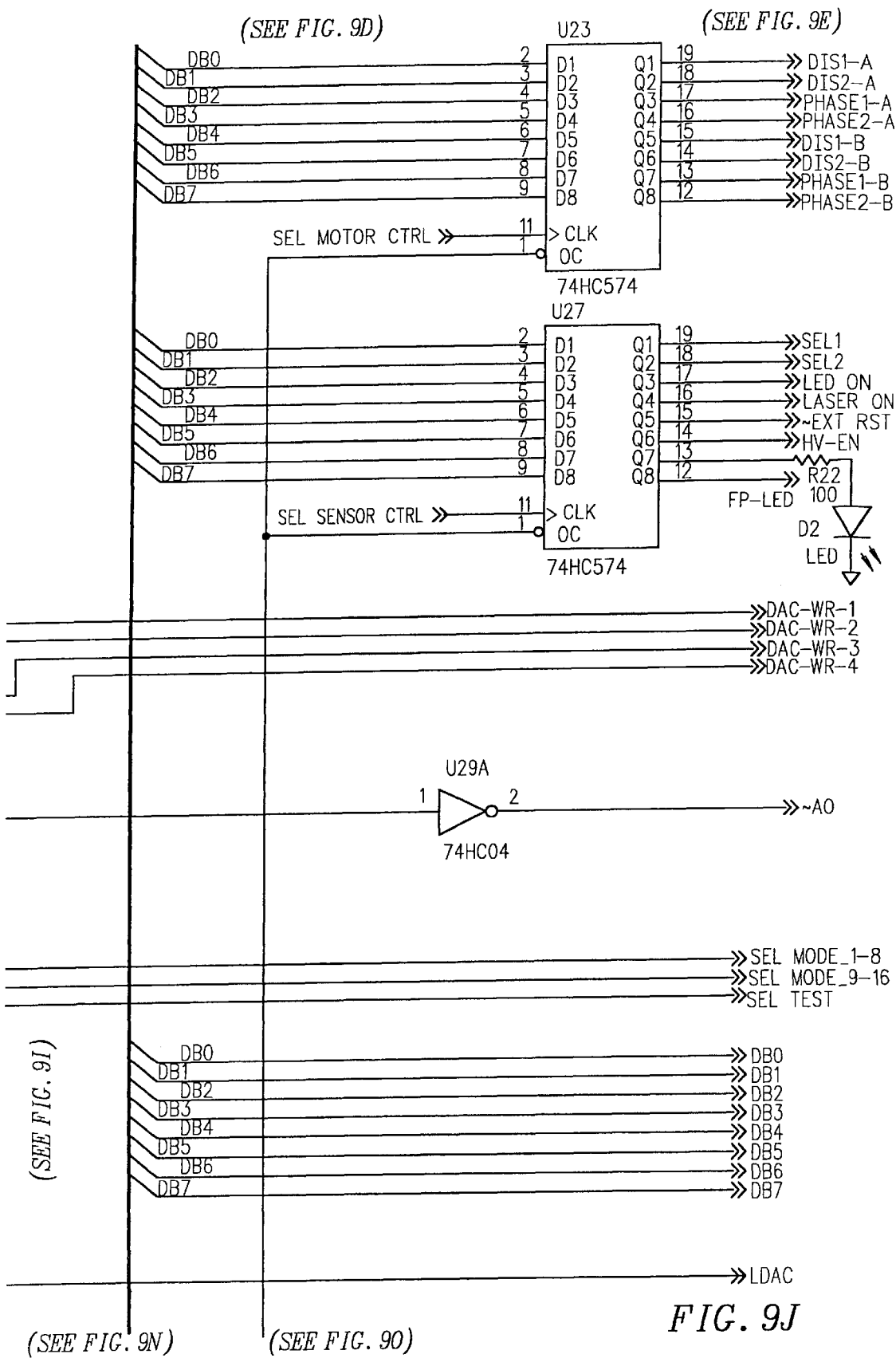
Figure 9K:
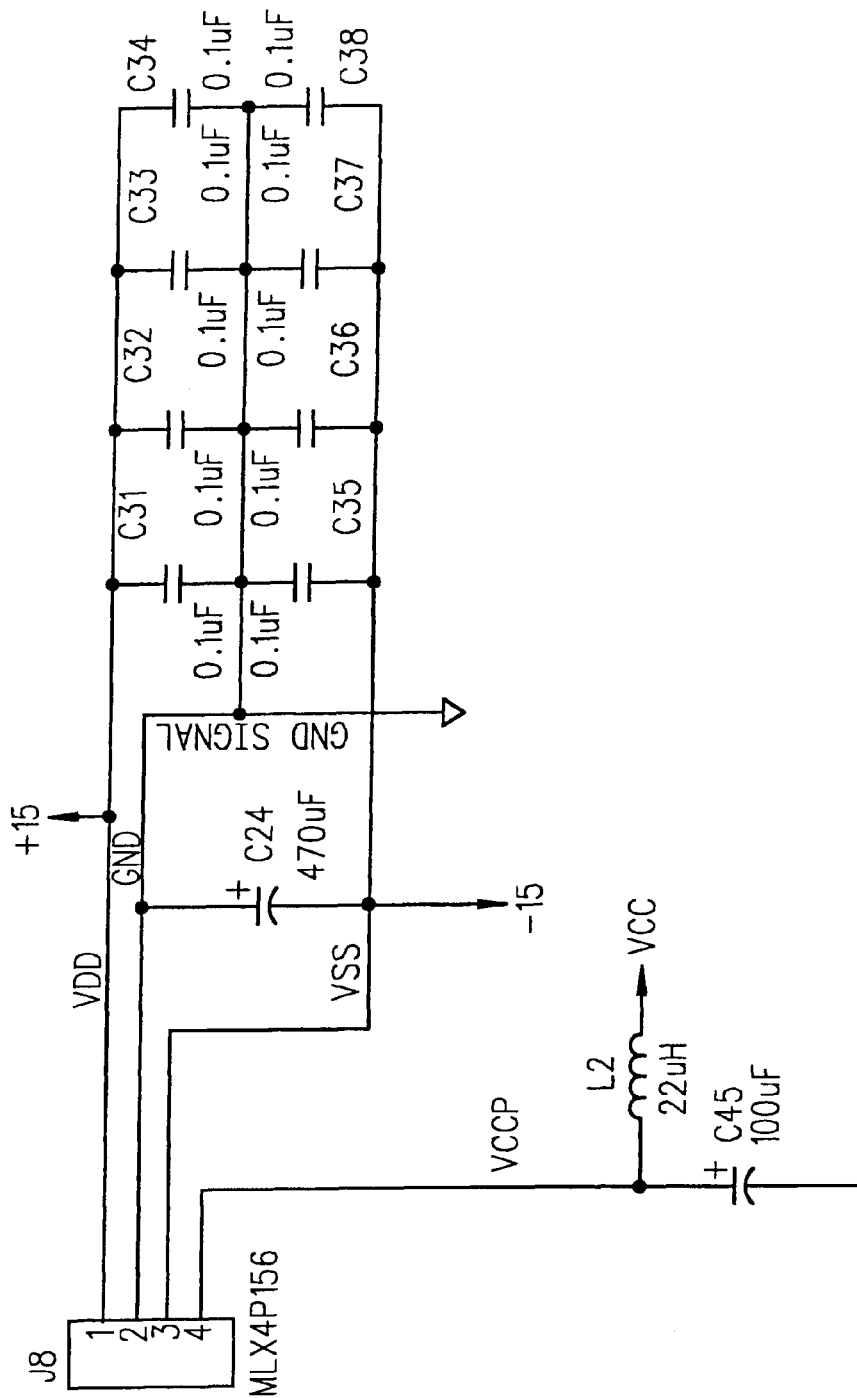
Figure 9L:
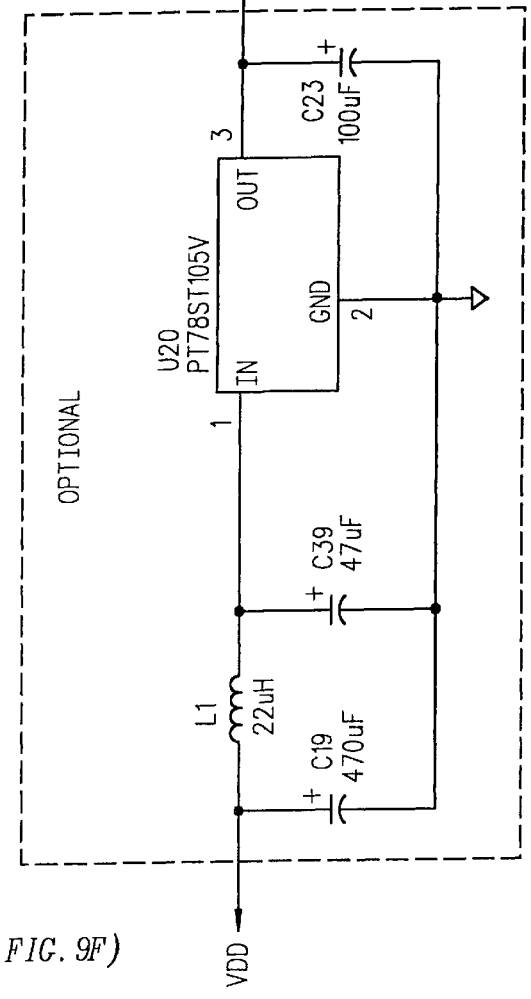
Figure 9M:
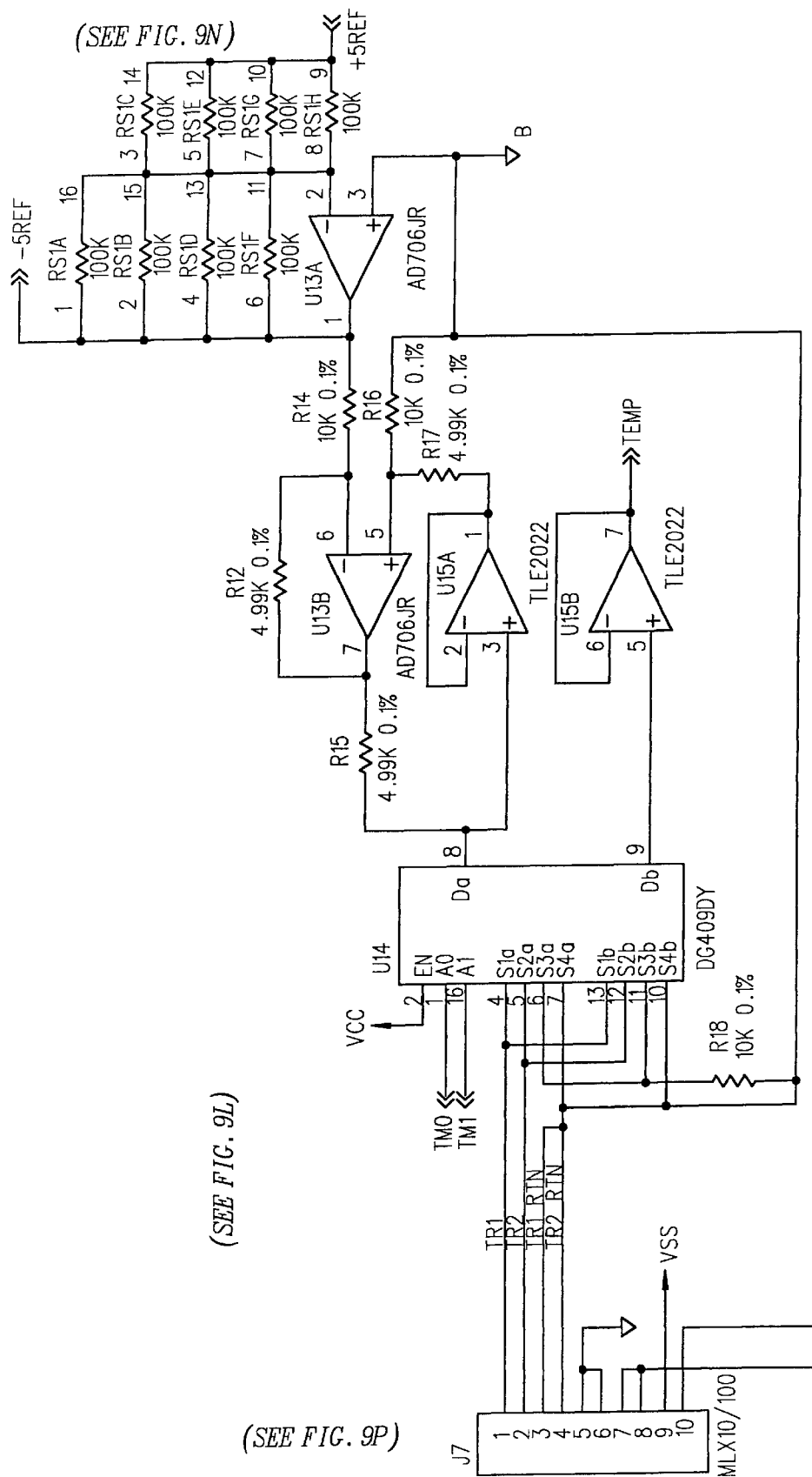
Figure 9N:
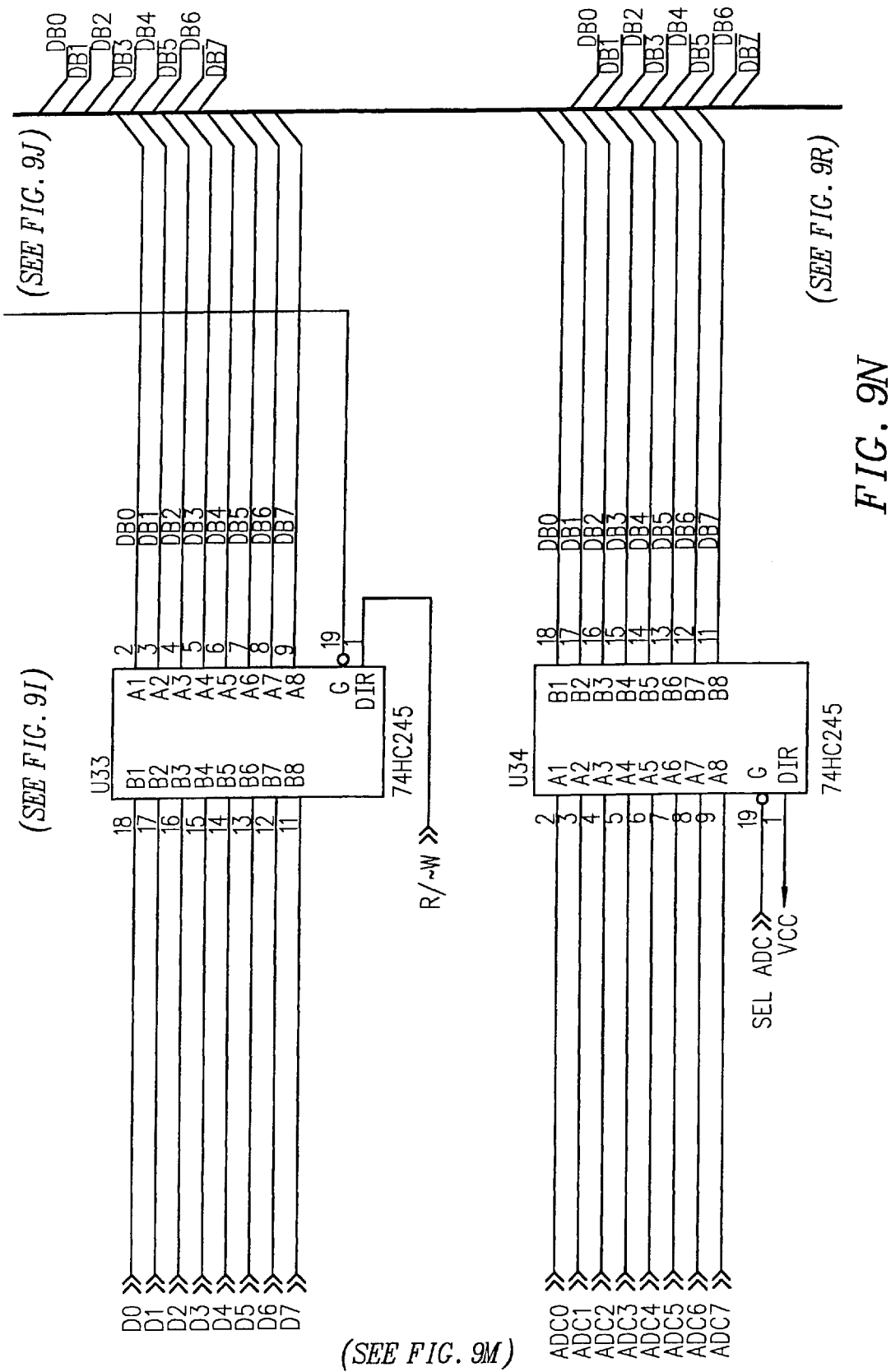
Figure 9O:
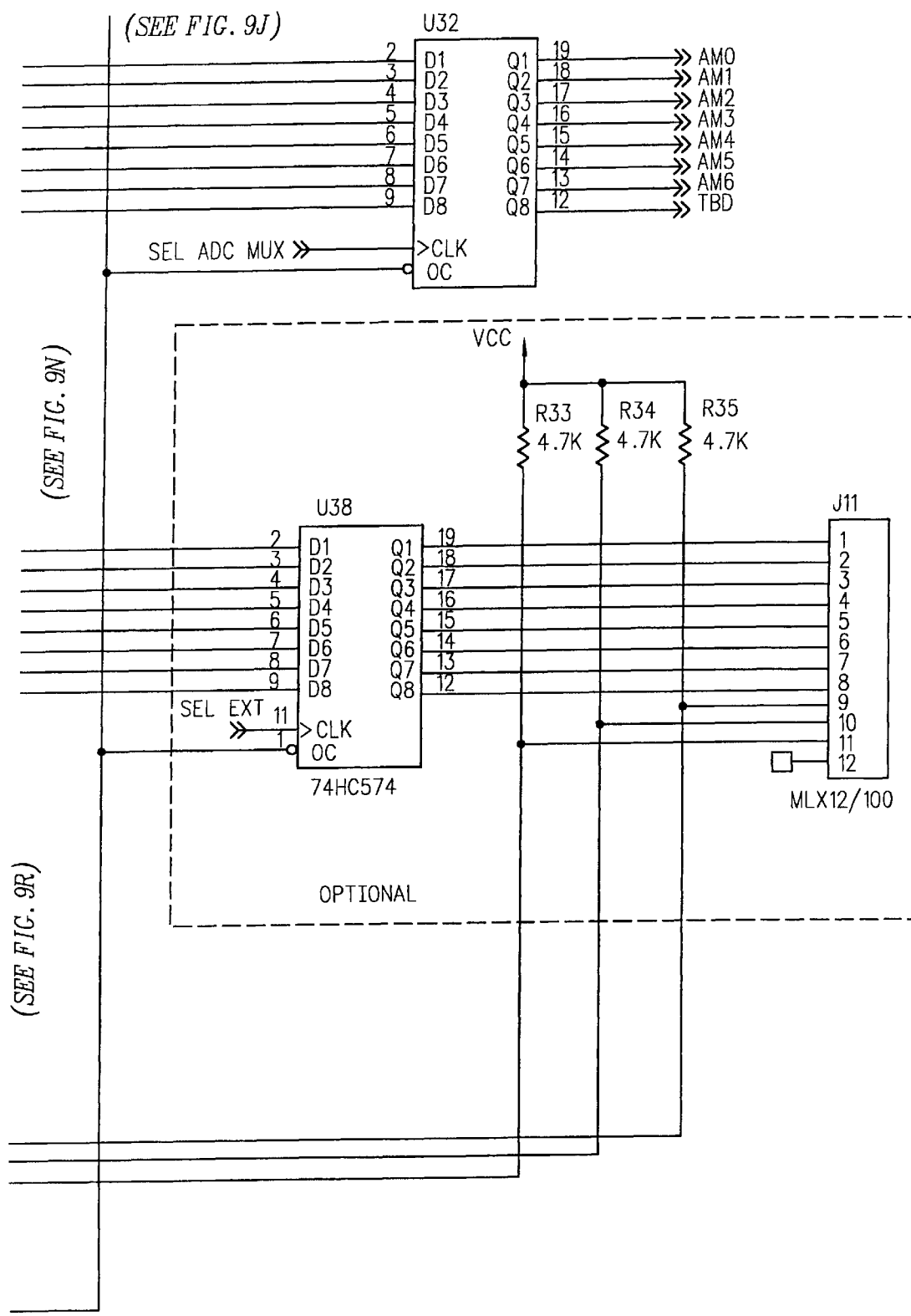
Figure 9P:
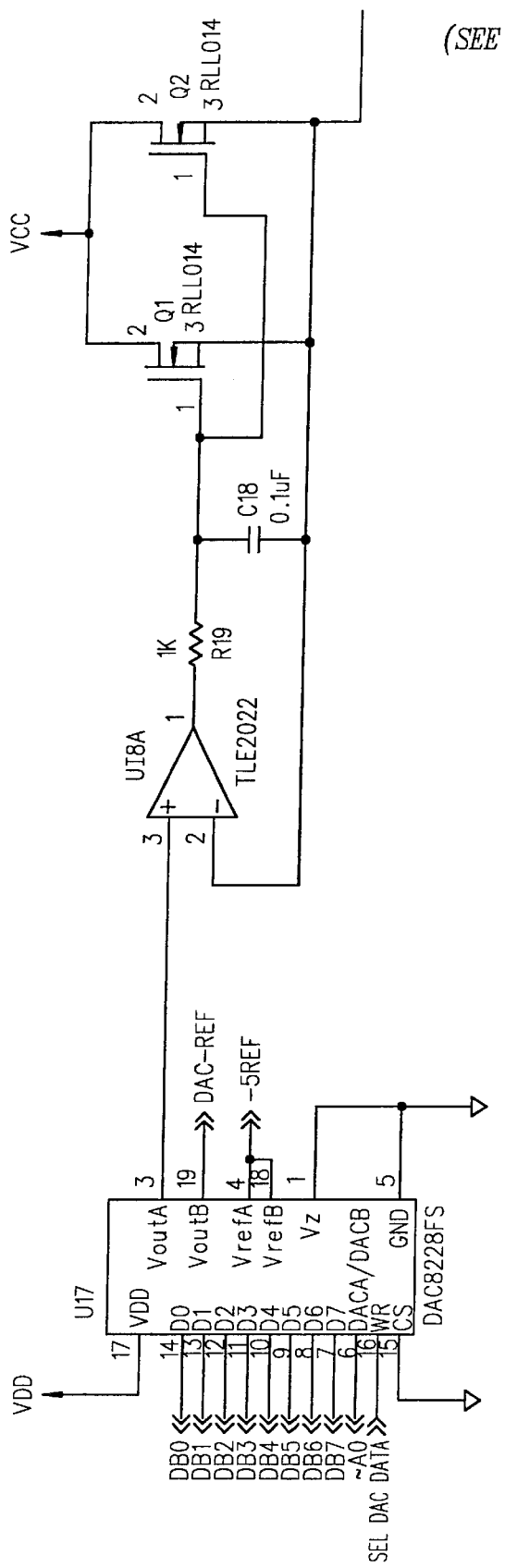
Figure 9Q:
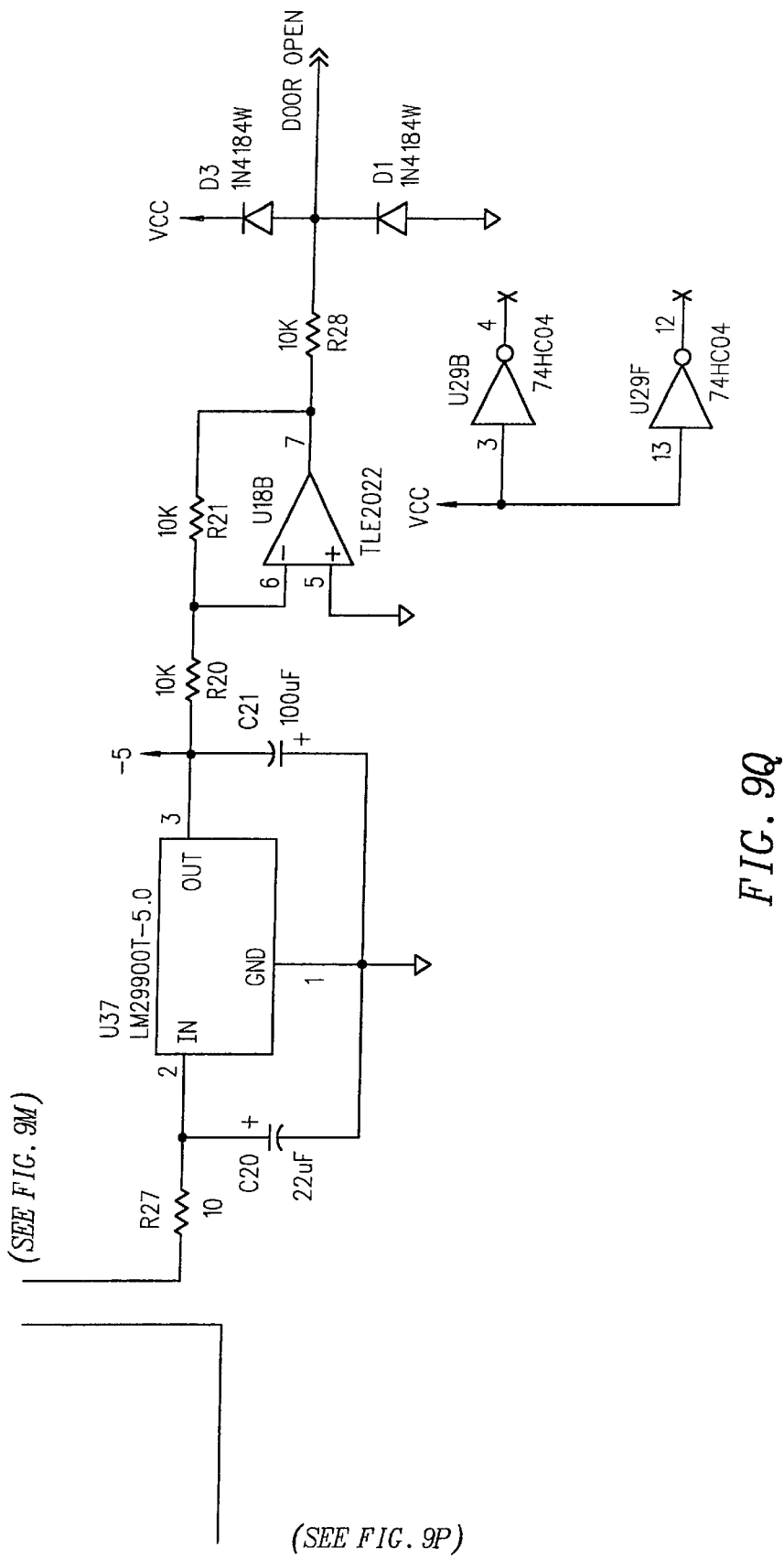
Figure 9R:
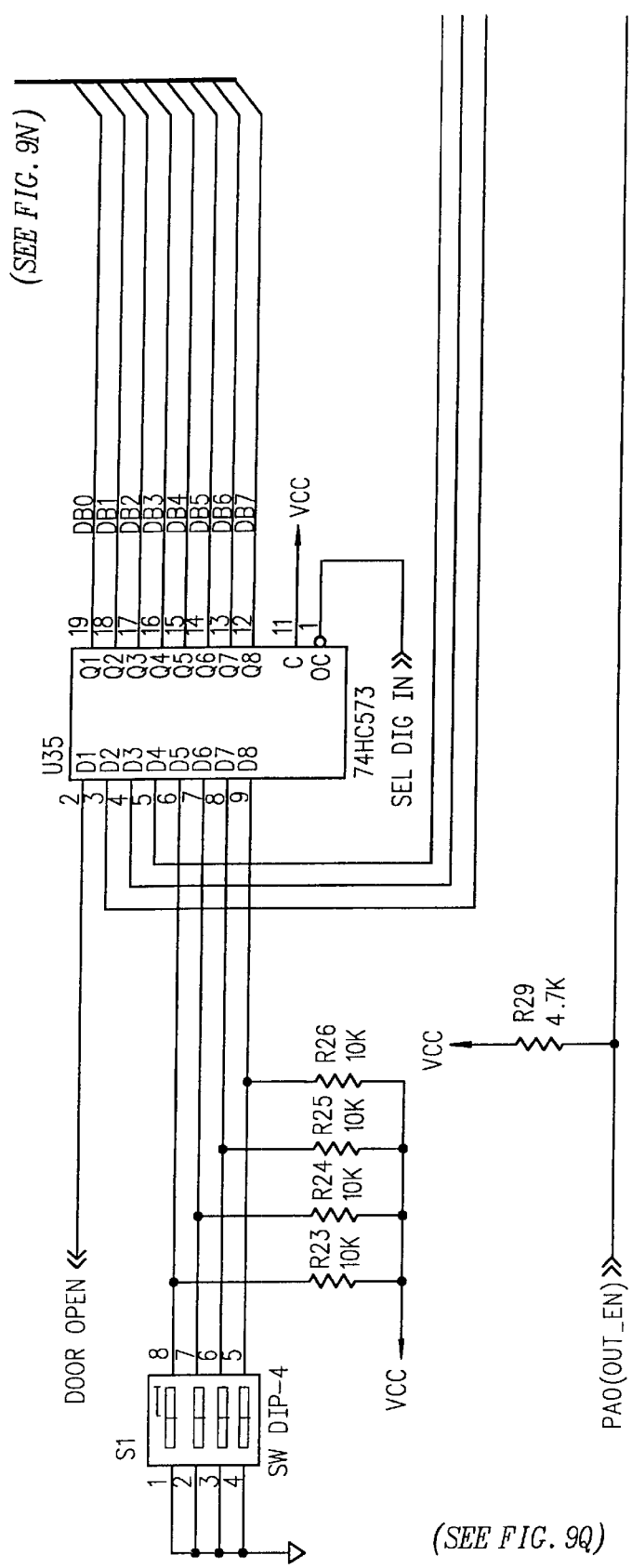

FIG. 6A is a perspective view of a reader assembly 189 and FIGS. 6B and 6C are exploded perspective views of the reader assembly 189 and the kinematic mounting assembly 80, respectively. Reader assembly 189 comprises the clam shell unit 24, the optics block assembly 50, the kinematic mounting assembly 80, and an assembly cover 188. The first and second stepper motors 81, 82 of the kinematic mounting assembly 80 and the L bracket 84 to which the motors 81, 82 are mounted form a wiggler assembly 180. As shown, the first and second stepper motors 81, 82 of the kinematic mounting assembly 80 utilize spindles. The clamshell unit 24 is positioned over wiggler assembly 180 and optic block assembly 50 such that objective 52 of optic block assembly 50 is in alignment with bore 36 defined within heat sink 33 of clamshell unit 24 (also shown in FIG. 2B).

Figures 2, 4D:
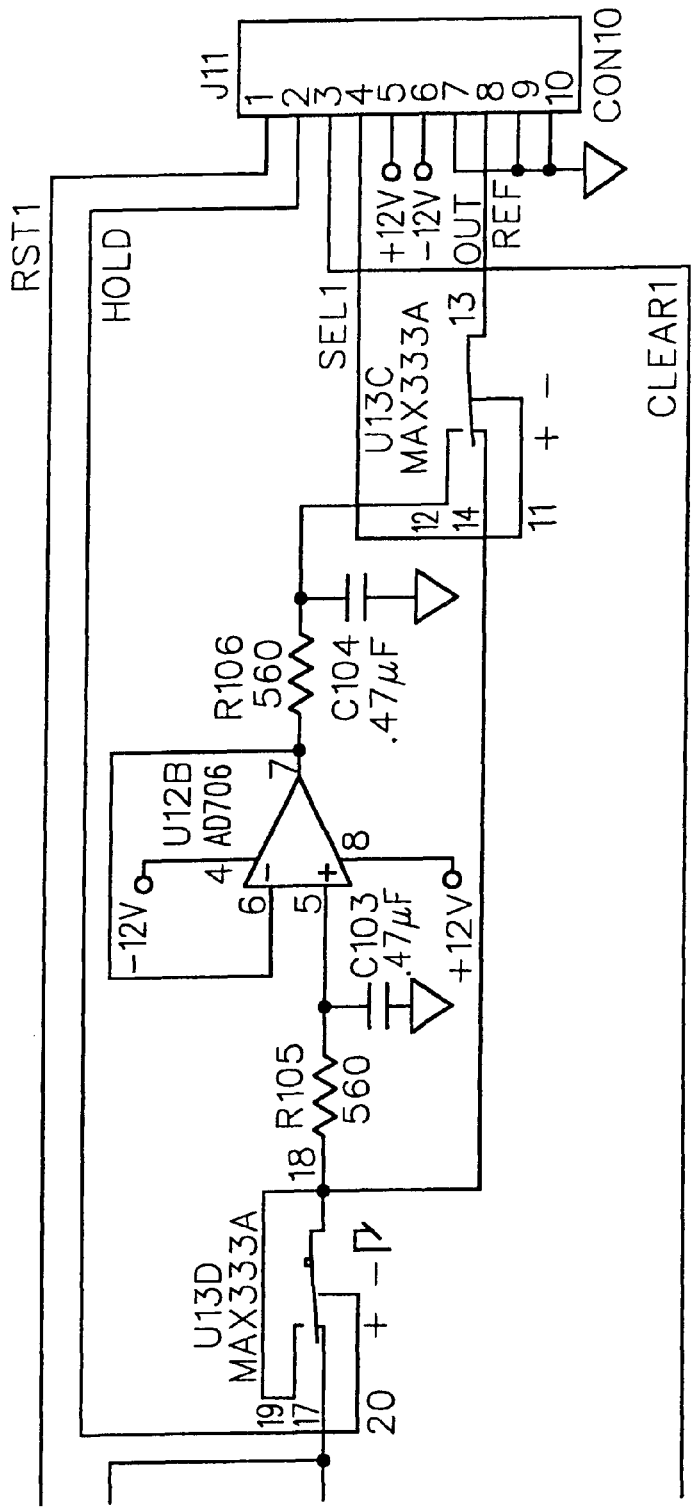
Figures 3, 4D:
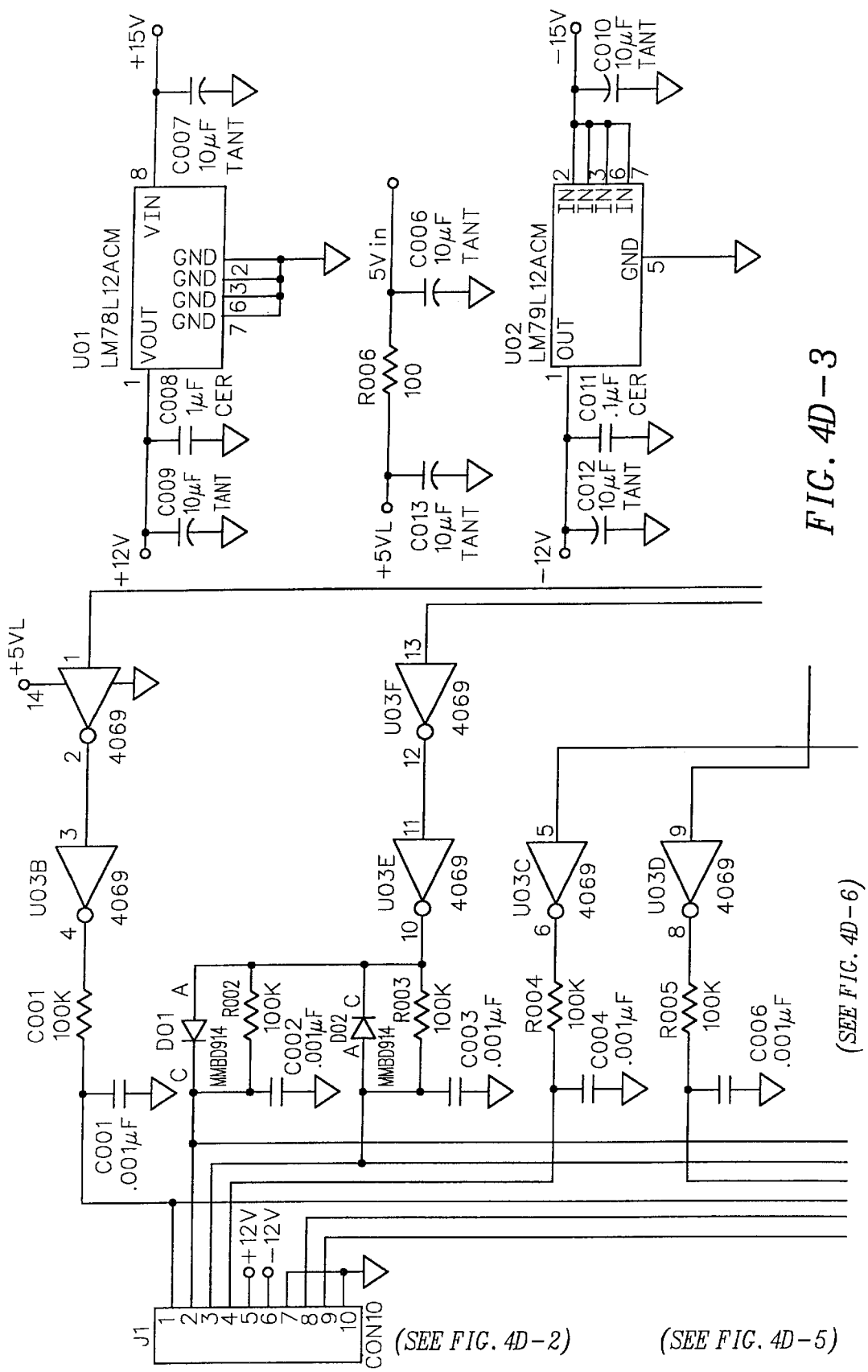
Figures 4, 4D:
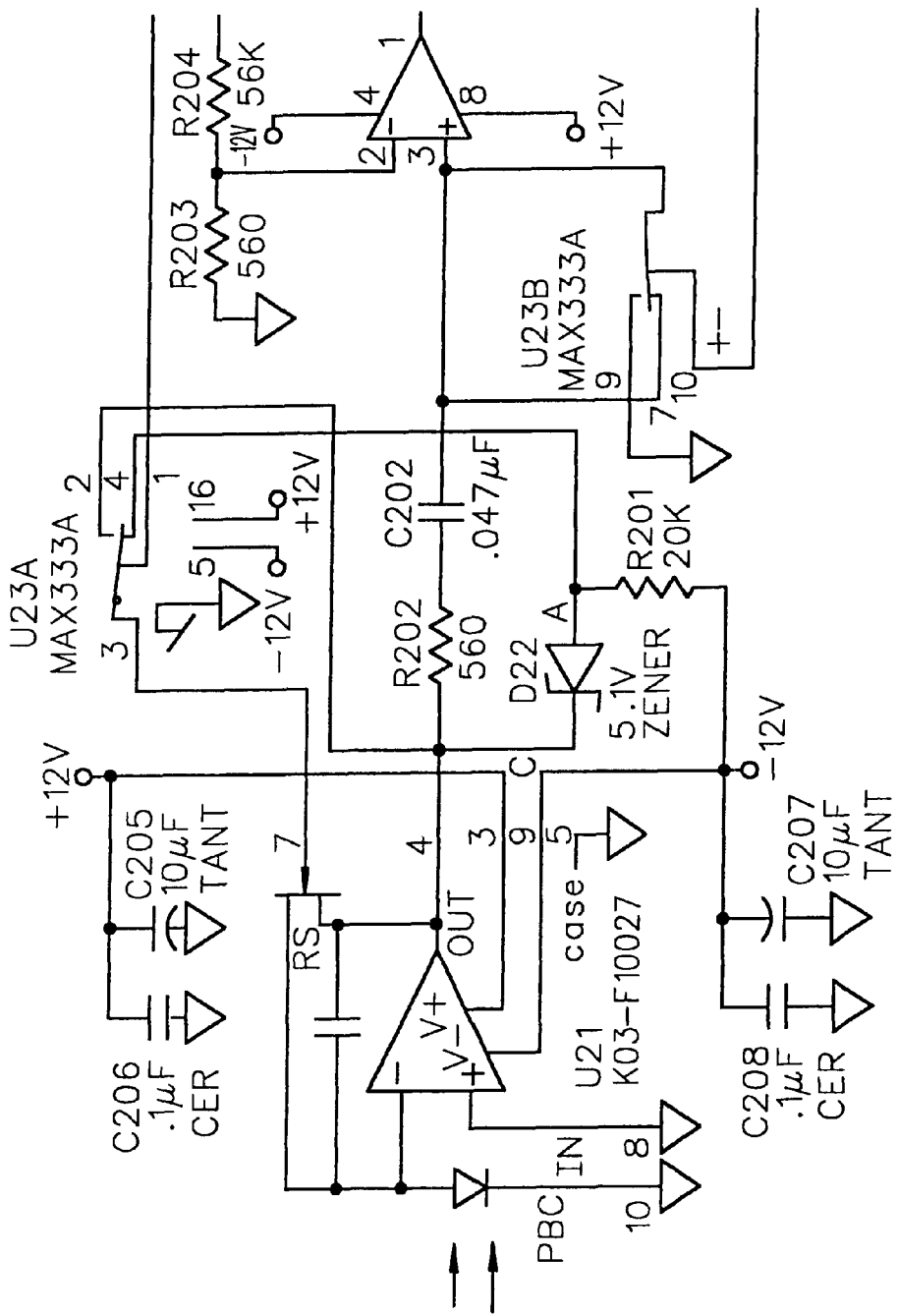
Figures 4, 4D, 5:
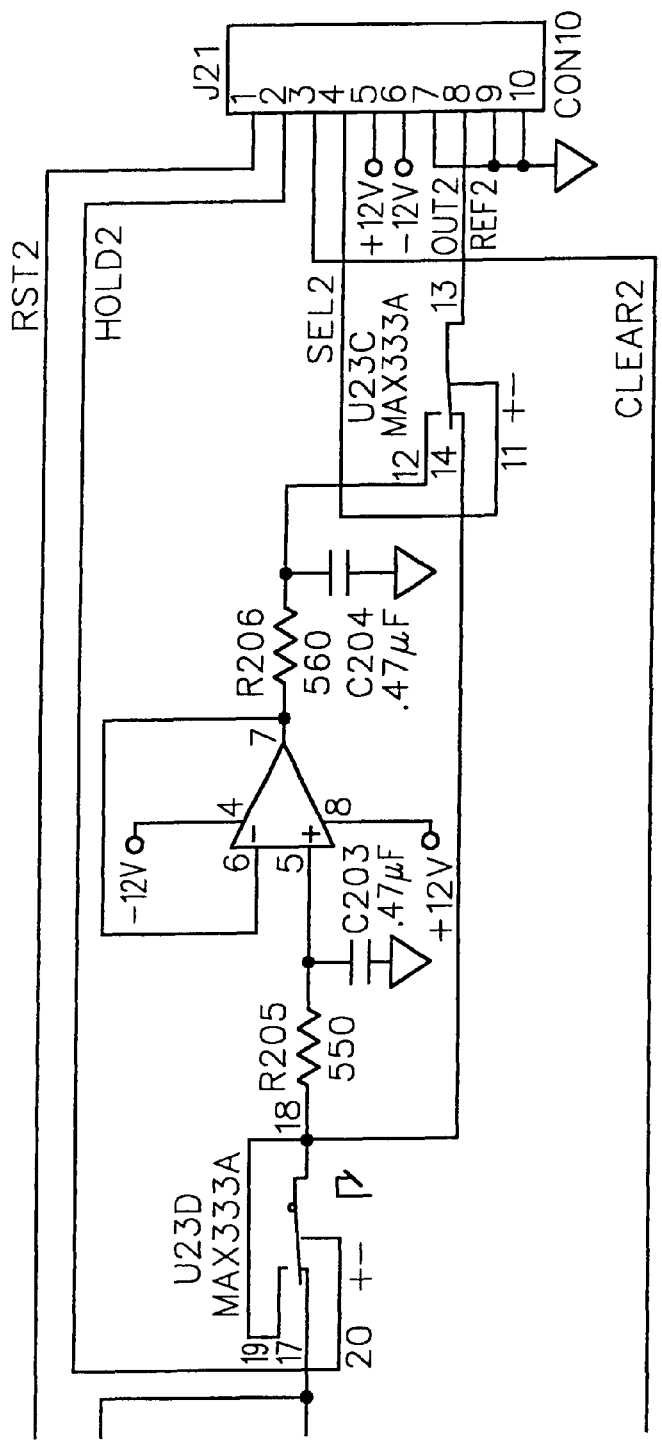
Figures 4, 4D, 5, 6, 7, 8:
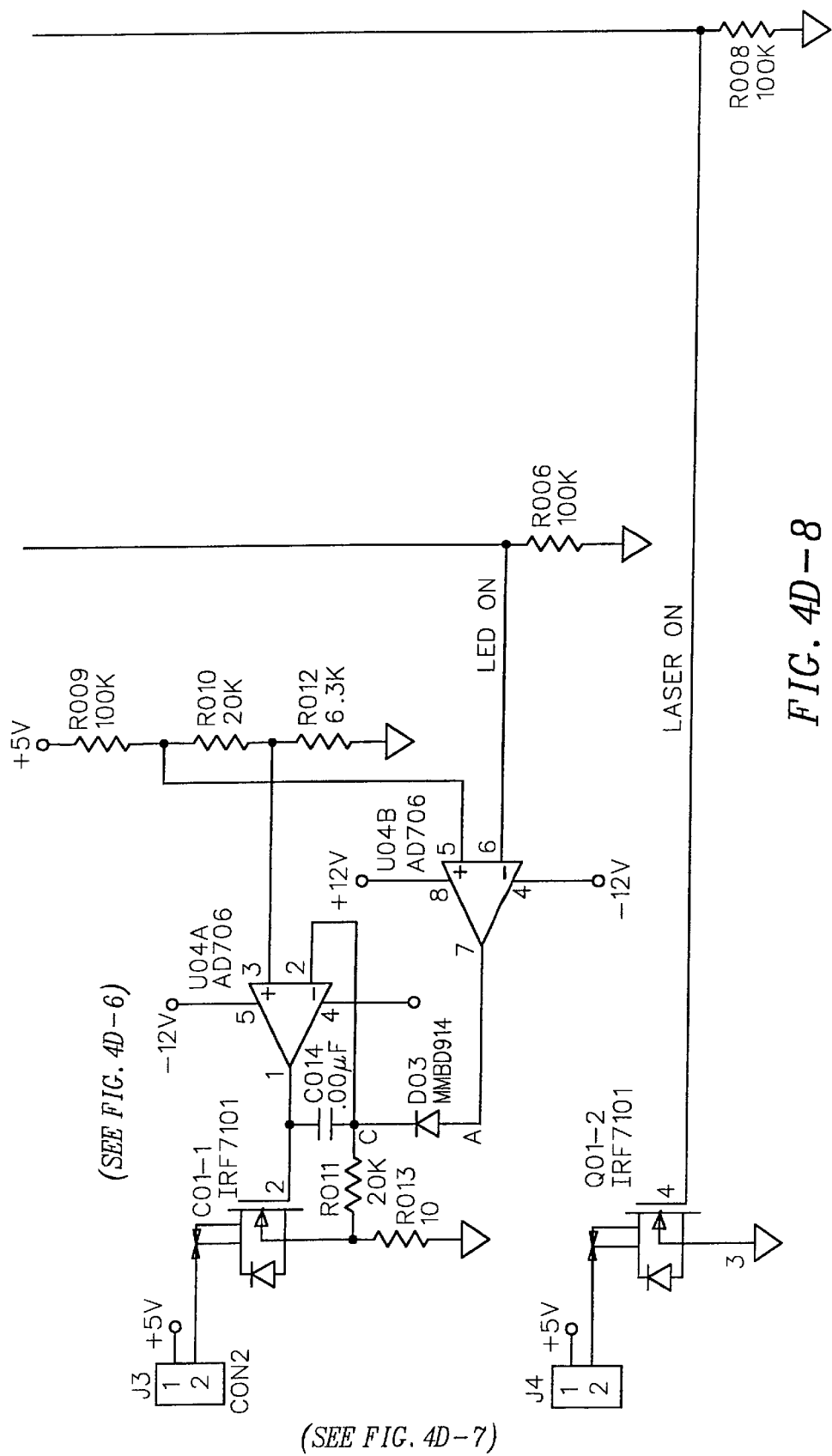
FIG. 7 is an exploded perspective view of a chassis assembly of the microfluidic controller and detector system illustrated in FIGS. 1A and 1B.
FIG. 8 is a schematic illustration of a microfluidic chip for use with the microfluidic controller and detector system illustrated in FIGS. 1A and 1B.

FIG. 7 is an exploded perspective view of a chassis 190 of microfluidic controller and detector system 20. Reader assembly 189, a control PCB assembly 191, a power supply 192 and a cooling fan 193 are typically coupled to chassis 190 in any suitable manner. A connector 194 provided connection via a communication channel 194a to a control system 198 such as a computer (shown in FIG. 1A). Two high voltage PCBs 195, 196 are optionally provided. A chassis cover 197 encloses chassis 190.

FIG. 8 is a schematic illustration of a microfluidic chip 100 for use with microfluidic controller and detector system 20, 20'. Microfluidic device 100, such as a microchip, is typically placed within clamshell unit 24 on base plate 32 (shown in FIG. 2) during operation. Microfluidic device 100 generally comprises a plate 102 defining a plurality of integrated network of channels 104 therein and a plurality of reservoirs 106–136 in various fluid communication with channels 104. Buffers, reagents, and/or samples to be analyzed are placed into one or more of reservoirs 106–136 for introduction into one or more of channels 104. Preferably, reservoirs 130, 132, 134 are waste reservoirs and reservoir 136 is a buffer reservoir. The fluids are transported from their respective reservoirs, either separately or together with other reagents from other reservoirs into a main analysis channel 138 and along the main channel to the waste reservoir 132, past a detection region (or window) 140.

The microfluidic device 100 is typically positioned within microfluidic controller and detector systems 20, 20' with its detection region or window 140 disposed in an optical path of the objective of the optic block such that the system is in sensory communication with detection region 140 of main analysis channel 138. The objective is preferably positioned at an appropriate distance for activating the fluorescent indicator within the test sample. As the sample passes the detection region 140, signals produced by the sample materials are detected by systems 20, 20'.

Detection window 140 is preferably transparent so that it is capable of transmitting an optical signal from main channel 138 over which it is disposed. Detection window 140 can merely be a region of a transparent cover layer, e.g., where the cover layer is glass or quartz, or a transparent polymer material, e.g., PMMA, polycarbonate, etc. Alternatively, where opaque substrates are used in manufacturing microfluidic device 100, transparent detection windows fabricated from the above materials is separately manufactured into the device.

Microfluidic device 100 preferably includes at least two intersecting channels and optionally includes three or more intersecting channels disposed within plate 102. Channel intersections can exist in a number of formats, including cross intersections, "T" intersections, or any number of other structures whereby two channels are in fluid communication. Microfluidic device 100 preferably has multiple sample introduction ports or reservoirs, for the parallel or serial introduction and analysis of multiple samples. Alternatively, microfluidic device 100 is coupled to a sample introduction port, e.g., a pipettor, which serially introduces multiple samples into the device for analysis.

The samples are typically transported along main analysis channel 138 and past detection window 140 by vacuum pressure and/or the application of electric fields such as with electrokinetic transport systems, for example. The electrokinetic transport system directs materials along the interconnected channels through the application of electrical fields to the material, thereby causing material movement through and among the channels, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electrostatic flow of fluid and material within a channel or chamber structure, which results from the application of an electric field across such structures.

In brief, when a fluid is placed into a channel which has surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at or near the fluid/surface interface, or a positively charged sheath surrounding the bulk fluid in the channel. Application of a current and/or a voltage gradient across the length of the channel causes the proton sheath to move in the direction of the current or the voltage drop, i.e., toward the negative electrode.

Microfluidic device 100 described herein is useful in performing a variety of analyses, such as characterization operations on biological macromolecules, e.g., proteins and/or nucleic acids, screening assays, electrophoretic separation of macromolecules (e.g., nucleic acids, proteins) and medium or high throughput screening assays, e.g., in pharmaceutical discovery and diagnostics as disclosed in U.S. patent application Ser. No. 08/8456,754, filed Apr. 25, 1997 and Published International Application No. WO 98/00231 which are hereby incorporated by reference in their entireties. The controller and detector system 20 in which the microfluidic device can be used is useful for detecting fluorescence induced by the buffers and/or samples from exposure of laser radiation to generate chromatographic data, for example. It is to be understood that the microfluidic device used with detection systems 20, 20' of the present invention may be different from those described herein without departing from the scope of the invention.

In operation, a separation buffer is typically first placed into, for example, buffer reservoir 136, and allowed to wick into channels 104, thereby filling the channels with the separation buffer. Samples that are to be analyzed are separately placed into one or more of reservoirs 106–128. The separation buffer, already present in reservoir 136, is typically also placed into reservoirs 130, 132 and 134. Movement of materials through the channels of the chip is accomplished by applying appropriate electrical currents and/or voltages through the channels to drive electrokinetic movement of the materials. Currents and/or voltages are supplied via electrodes 45 (shown in FIGS. 3B and 3C). Each electrode generally corresponds to a reservoir such that, in the exemplary embodiment shown and described, there are sixteen electrodes corresponding to sixteen reservoirs.

Through the application of appropriate electric inputs, a first sample material is transported or electrokinetically transported from its reservoir, e.g., reservoir 106, to and through a main injection intersection 142 for main channel 138, via channels 140a and 140b. In one embodiment, this can be accomplished by applying a current between reservoirs 106 and 134. Low level pinching currents are typically applied at intersection 142 in order to prevent diffusion of the sample material at the intersection, e.g., by supplying a low level of current from reservoirs 132 and 136 toward reservoir 134 (see, e.g., WO 96/04547, incorporated in its entirety by reference herein).

After a short period of time, the application of current is switched such that material in intersection 142 is electrokinetically transported through main analysis channel 138, e.g., by applying a current between reservoirs 136 and 132. Typically, a slight current is applied after the injection to pull materials in channels 140b and 140c back from intersection 142, to avoid leakage into main channel 138.

While the first sample is transported through main channel 138, a second sample to be analyzed is typically preloaded by transporting the second sample material from its reservoir, e.g., reservoir 108, toward preload reservoir 130 through preload intersection 144. This allows for only a very short transit time to move the sample material from its preloaded position to injection intersection 142. Once analysis of the first sample is complete, the second sample material is typically transported across injection intersection 142 and injected through main analysis channel 138, similar to the process described above. This process is preferably repeated for each sample loaded into chip 100. The desired analysis operations are carried out in analysis channel 138, such as electrophoretic separation and screening interactions. Although generally described as incorporating electrokinetic material transport system, it will be appreciated that other systems can optionally be employed in addition to, or in lieu of such an electrokinetic system. For example, a vacuum source or pump is optionally provided in main unit 22 with connection via clamshell 24.

A number of the components that are used in conjunction with the present invention have been described in commonly owned, copending applications, including, e.g., U.S. application Ser. No. 09/165,704, filed Oct. 2, 1998, U.S. application Ser. No. 08/919,707, filed Aug. 29, 1997, and Published International Application No. 98/05424, each of which is incorporated herein by reference in its entirety.

As noted above, the interaction of the first and second components is typically accompanied by a detectable signal. Generally, monitoring of the signals produced by the sample materials at the detection window is achieved by placing a laser light source at an appropriate wavelength for activating the fluorescent indicator within the test system. Fluorescence is then detected using the lens assemblies in combination with the detector PCBs as described above with reference to optic assembly 50. The signals are preferably monitored by objective 52 (shown in FIGS. 4B and 4C). These signals are viewed by the lens assemblies which transmit the signals to their corresponding detectors. The PCBs then transmit the signals to the computer. The computer can then be used to analyze the signals and create various outputs, such as graphs, tables and charts. Furthermore, computer 198 (shown in FIG. 1A) is typically used to control microfluidic system 20 or 20'. Commands are input, through appropriate input means such as a keyboard or a mouse, to the computer which then transmits commands to control PCB assembly 191.

Thus, the present invention provides a microfluidic detector and controller system that works with a microfluidic chip which is optionally constructed of two similarly bonded planar glass substrates. Referring again to FIGS. 2 and 3A–3C, the microfluidic chip is typically placed onto base plate 32 within a clamshell configuration that includes controlling electrodes 45 that mate with holes (not shown) provided in an upper substrate of microfluidic chip 100. Closure of clamshell lid 43 places the mating array of electrodes 45 into contact with the various reservoirs and thus the fluids contained within microfluidic chip 100. Electrical inputs are generally delivered via electrodes 45 to the various reservoirs and serve to direct material transport through the interconnected channels by vacuum pressure, electrophoretic and/or electrosmotic movement, for example.

The channel network is filled with a separation medium. Preferably the separation medium used is a low viscosity solution of polydimethacrylade-co-acrylic acid. The DNA is labeled with the intercalating fluorescent dye "Syto-66 Super TM" which is available from Molecular Probes. Nucleic acid fragments are separated as they travel through the separation or main analysis channel due to their differing electrophoretic mobilities. These fragments take up the dye within the separation medium.

The fluorescent intercalating dye, associated with the fragments, are typically detected by objective 52 with light emitted from light source 58a and reflected off of mirror 66a and passed through mirror 66b, as shown in FIGS. 4A–4C. Alternatively, second light source 58b can transmit a blue light though objective 52 via lens assembly 60b and mirrors 66c, 66b. Light is transmitted back and detected by one of detectors 74a, 74b. One or both of these light sources and/or other light sources which may be alternatively or additionally provided are optionally used to activate the dye that is associated with nucleic acids within the main analysis channel.

Figure 10:
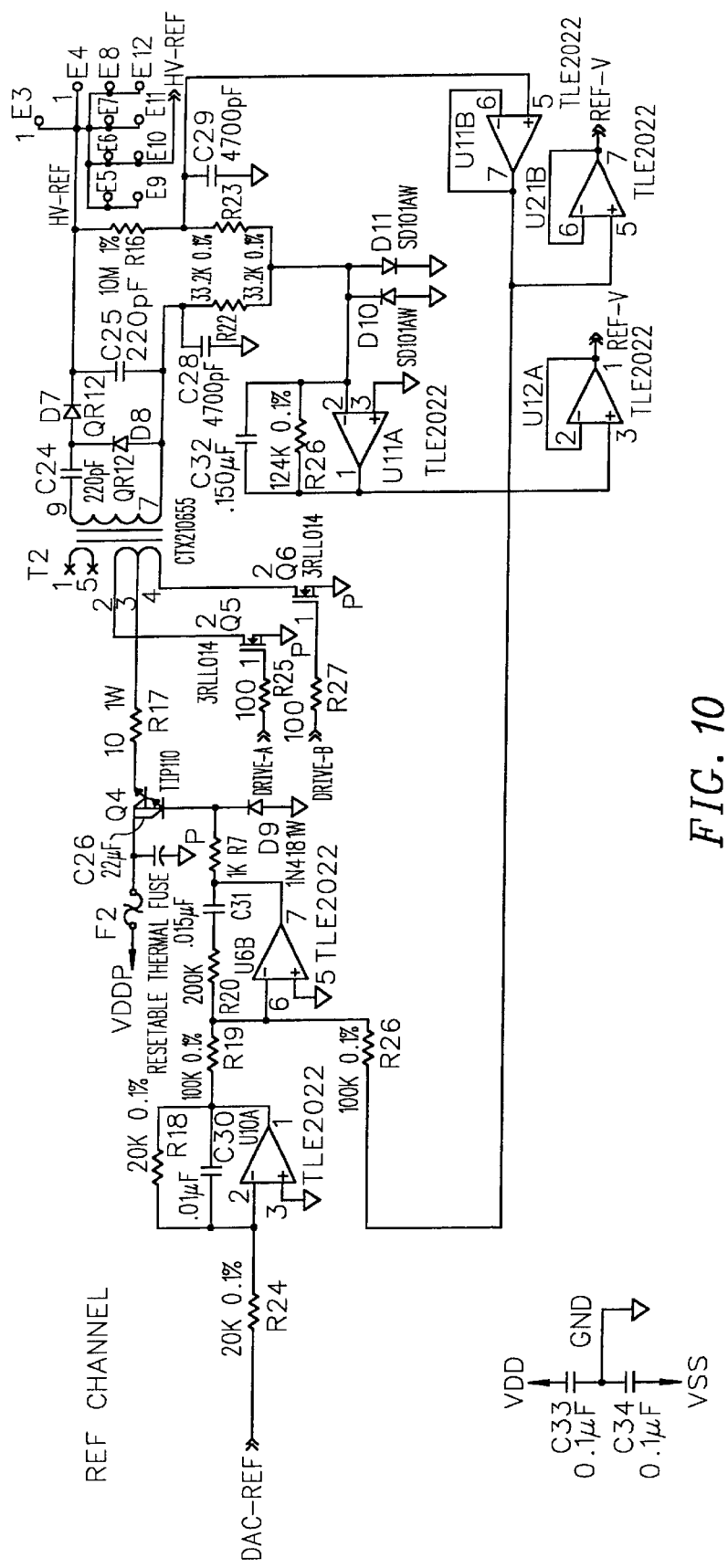
FIG. 10 is a schematic of the reference high voltage channel control circuitry board 195 for calibrating an electrical source channel.
Figure 11:
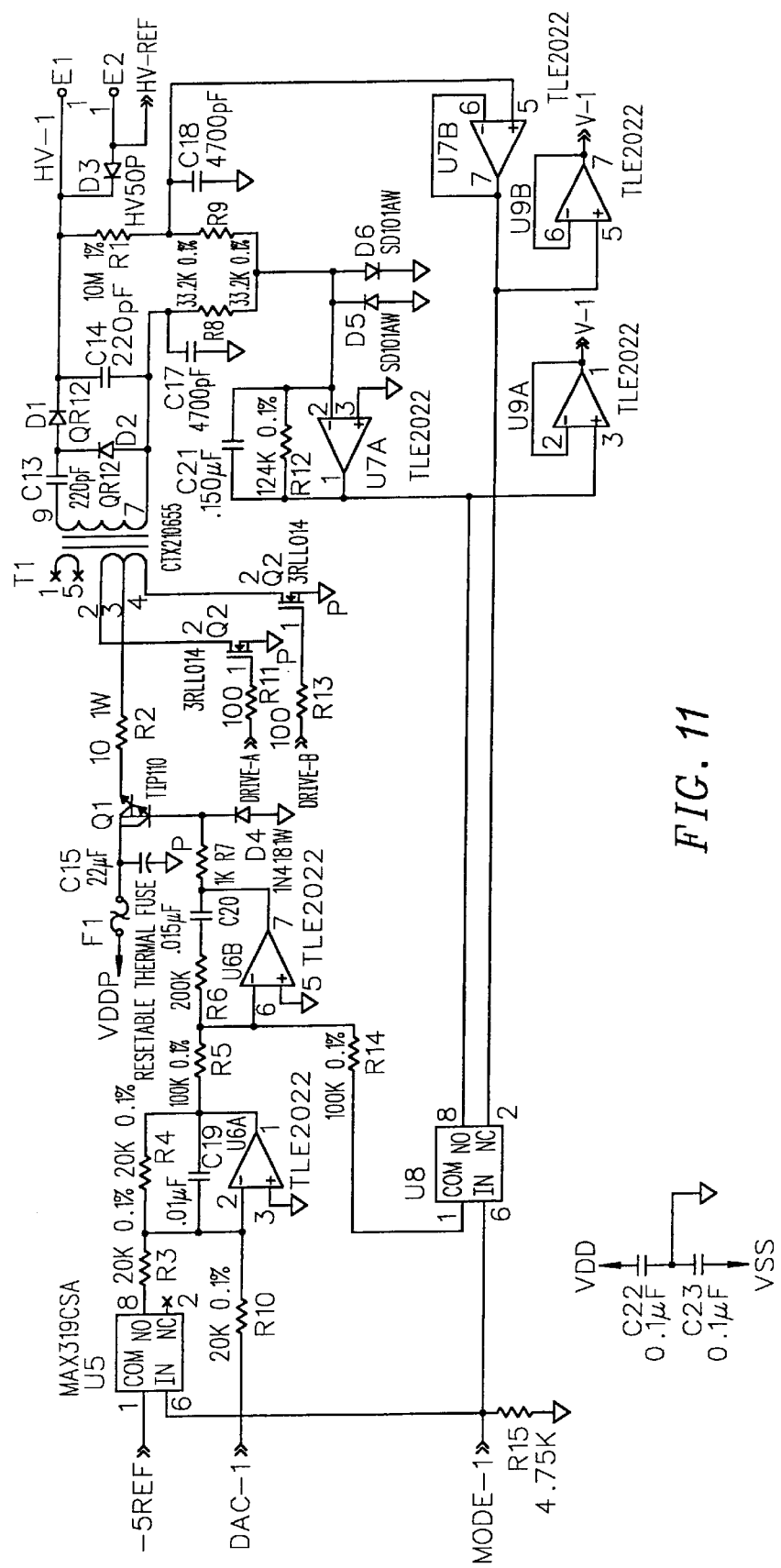
FIG. 11 is a schematic of a control circuitry board for each high voltage source channels.
Figure 12A:
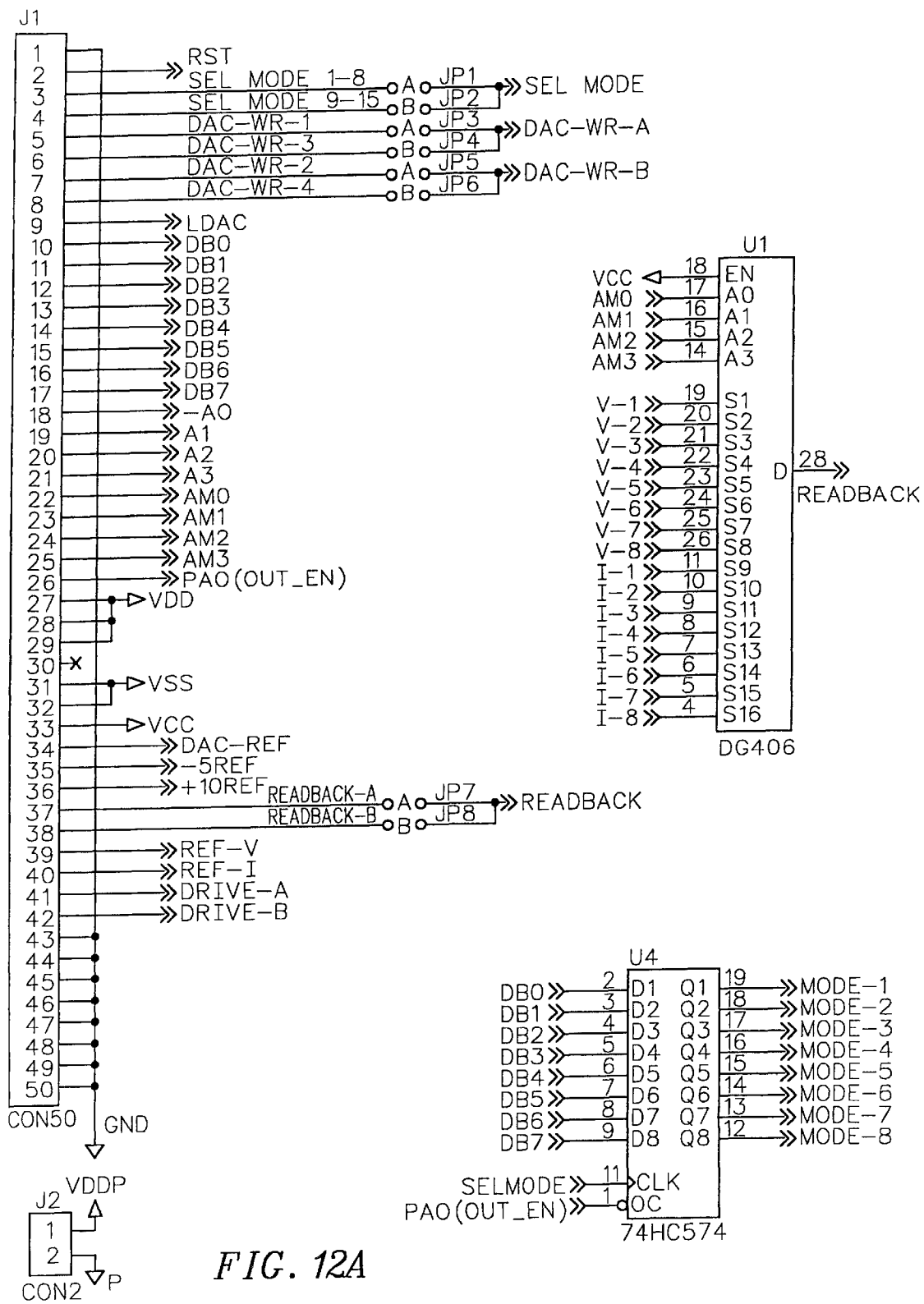
FIG. 12 is a schematic of a control circuit for a high voltage board.
Figure 12B:
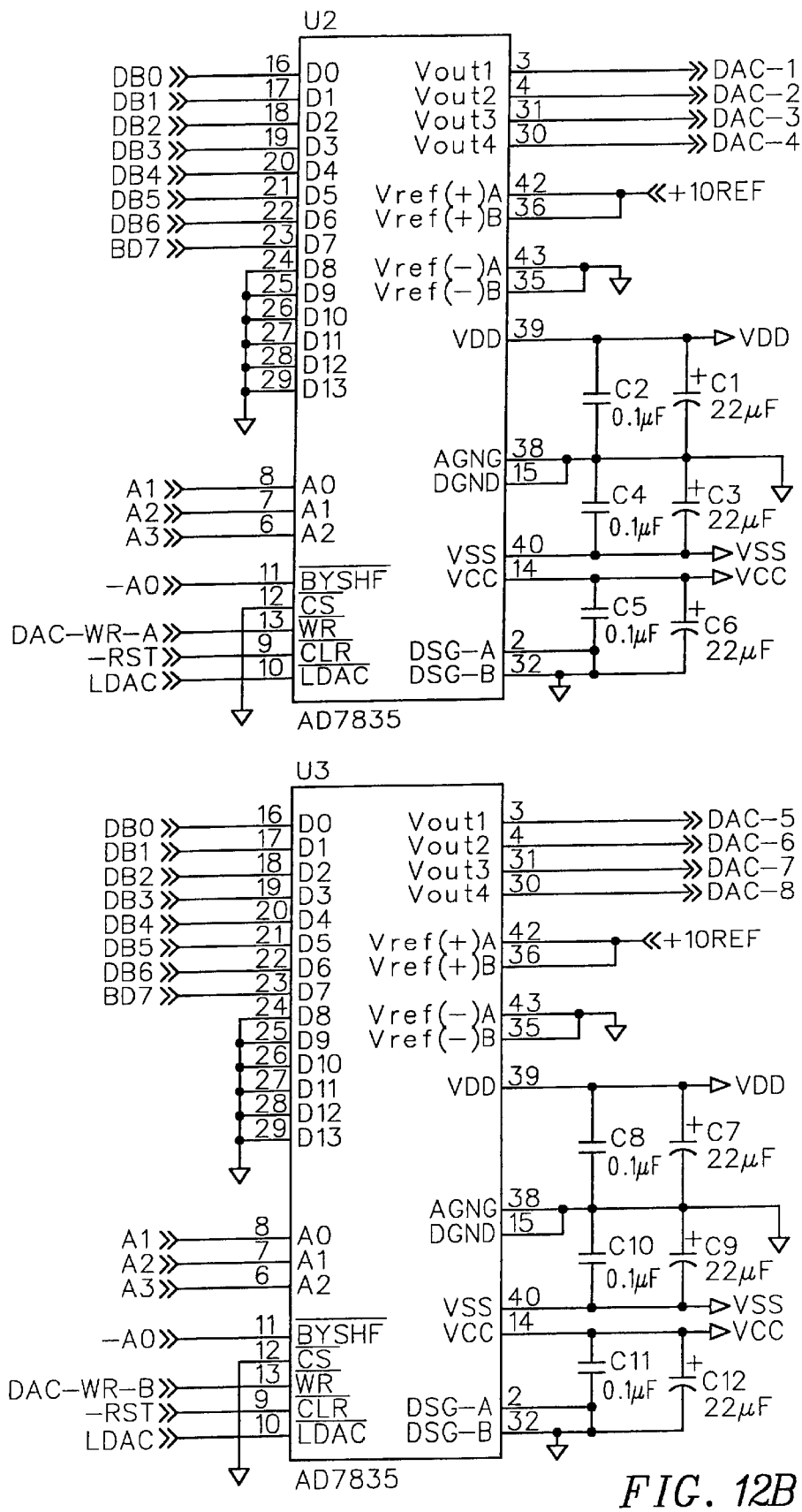

FIG. 9 is a schematic of an embodiment of a system control circuitry board 191. FIG. 10 is a schematic of the reference high voltage channel control circuitry board 195 for calibrating all electrical source channels. FIG. 11 is a schematic of a control circuitry board 196 for each of the 16 high voltage source channels. FIG. 12 is a schematic of a control circuit for a high voltage board.

FIG. 13 is a simplified schematic illustrating one embodiment of circuitry 200 for high voltage control PCB assembly of a reference channel 202 and various high voltage electrode channels 204, 206, 208, 210 for use with microfluidic controller and detector system 20 or 20'. Each high voltage electrode channel is connected via an electrode to a reservoir defined in the microfluidic chip. As described above, each electrode generally corresponds to a reservoir such that, in the exemplary embodiment shown and described, sixteen electrode channels are provided to correspond with the sixteen electrodes which in turn correspond to the sixteen reservoirs. The reference channel is an extra channel provided to enable calibration of the electrode channels. Although shown with four electrode channels, circuitry 200 may include any number of two or more electrode channels in addition to reference channel 202.

Electronic circuits drift, whether due to aging, temperature and/or humidity changes, and/or other causes. Electronic drifts affect the performance of the electronic circuit. For example, for microfluidic controller and detector system 20 or 20', it is highly desirable to tightly control the voltage or current applied to the reservoirs via the electrodes. Generally, electronic drifts that match, i.e. drift by a same ratio, for all electrode channels do not significantly degrade the performance of the electronic circuit. However, if the applied voltage or current to one reservoir increases by, for example, 1% while the applied voltage to another reservoir decreases by, for example, 1%, such electronic drift could lead to chemical cross-talk between the contents of different reservoirs. Further, it is generally difficult to provide high voltage resistors that are stable over time and temperature for the level of precision desired for the microfluidic controller and detector system. Such high voltage resistors are used in resistor voltage dividers for each high voltage channel to measure and set the voltage of the channels.

Thus, the reference channel is provided in the circuitry for high voltage control PCB assembly as an extra channel for use in calibration of the electrode channels. Preferably, a calibration scheme or process is executed prior to each test or run to analyze the microfluidic chip. Because the circuitry for the reference channel is utilized only once for each test or run, effects of aging on the reference channel circuitry is reduced as compared to the electrode channels. Further, although described in terms of microfluidic controller and detector system 20 or 20', the provision of the reference channel and the calibration process is optionally utilized in any system to ensure that voltages and/or currents for a plurality of channels match.

As shown in FIG. 13, reference channel 202 generally comprises a high voltage generator 212 which receives a DAC set-point output 214 as input. Reference channel 202 further includes a voltage divider comprising serially coupled first and second high voltage resistors 218, 220. The voltage divider is coupled in parallel to high voltage generator 212. A voltage 222 is taken between two nodes of second high voltage resistor 220. In addition, a current 224 is taken between a node 230 coupled to high voltage generator 212 and second high voltage resistor 220 and ground. Output of the reference channel OUTREF or output of each electrode channels OUT1, OUT2, etc. is taken at node 228. Reference channel 202 is coupled to each of electrode channels 204, 206, 208, 210 via a low leakage high voltage diode 226. Each high voltage electrode channels 204, 206, 208, 210 is of generally identical construct as reference channel 202, except that they have a voltage or current mode select signal 216 as inputs.

FIG. 14 is a simplified schematic showing the feedback loop circuitry for first channel 204 in greater detail. As noted above, the circuitry for the high voltage electrode channels and for reference channel 202 are of generally identical construct. As shown, high voltage generator 212 of first channel 204 generally includes an integrator 232, a transformer with voltage doubler 234, a diode 236, and an amplifier 238 for converting a current to voltage. High voltage generator 212 is controlled by a feedback loop that regulates output based on DAC setpoint output 214 and voltage and current readings 222, 224. Voltage reading 222 and current reading 224 are sampled by an analog-to-digital converter to generate a digital value representation of the actual voltage and current on the output 240.

Amplifier 238 is operated in such a way that node 230 is at virtual ground. During operation, the electrode channels are optionally set in all the same mode or in different modes. Because reference channel 202 preferably operates only in voltage mode, a portion of the circuit, e.g., switch 216, need not be provided.

During normal operation or analysis of samples in the microfluidic chip, reference channel 202 is shut off such that no significant current flows between the reference channel and each of the high voltage electrode channels so long as the voltage at each high voltage electrode channel is at a positive or 0 voltage. In contrast, during calibration, voltage at reference channel 202, i.e., voltage at reference node 228, is set to a positive voltage at least an amount of a voltage drop across diode 226 greater than voltage of one or more high voltage electrode channels such that current can flow to those one or more of the high voltage electrode channels.

The following is a description of an exemplary calibration process although any other suitable calibration processes can optionally be utilized and numerous modifications can be made to achieve similar calibration results.

First, reference channel 202 and all the electrode channels are shut off. The voltage and current $V_{RefReadOffset}$, $I_{RefReadOffset}$ of reference channel 202 are measured. The voltages and currents $V_{ChNReadOffset}$, $I_{ChNReadOffset}$ of each electrode channel N, where N ranges from 1 to the number of electrode channels, such as sixteen, are measured.

Next, voltage at node 240 of all electrode channels are set to a 1200V set point voltage or $V_{1.2\ kVSetPoint}$ and voltage at node 228 of reference channel 202 is set to a 1000V set point voltage or $V_{1\ kVRefSetPoint}$. Because the actual 1000 V reference channel set point voltage may not be exactly equal to 1000 V, the 1000 V set point voltage is represented by $V_{1\ kVRefSetpoint}$. Similarly, because the actual 1200 V electrode channel set point voltage may not be exactly equal to 1200 V, the 1200 V set point voltage is represented by $V_{1.2\ kvsetpoint}$. In addition, because the voltage of reference channel 202 is lower than the voltage of electrode channels 204–210, no current flows between the reference channel and any of the electrode channels. The output voltage $V_{ChNReadB}$ at node 222 of each of the electrode channels is measured.

The current of each electrode channel is then individually set to a $-1.25\mu A$ set point current or $I_{-1.25\ \mu ASetPoint}$ while maintaining voltages at node 240 of all other electrode channels at $V_{1.2\ kVSetPoint}$. Because the actual electrode channel set point current may not be exactly equal to −1.25 µA, the −1.25 µA set point current is represented by $I_{-1.25\ \mu ASetPoint}$. The electrode channel current setting renders each corresponding diode 226 of the electrode channel forward biased such that voltage at node 240 of the electrode channel is at a voltage equal to the voltage at node 228 of reference channel 202 less a voltage drop across diode 226. The voltage $V_{chNReadC}$ and current $I_{CbNReadC}$ are measured for each electrode channel. The voltage $V_{RefReadC}$ and current $I_{RefReadC}$ are also measured for reference channel 202. Generally, the reference current is read for each channel reading while the voltage reference is read only once for all the channel readings.

Next, the current of each electrode channel is individually set to a $-3.75\mu A$ set point current or $I_{-3.75\ \mu ASetPoint}$ while maintaining voltages at node 240 of all other electrode channels at $V_{1.2\ kvsetpoint}$. Again, because the actual electrode channel set point current may not be exactly equal to −3.75 µA, the −3.75 µA set point current is represented by $I_{-3.75\ \mu ASetPoint}$. The electrode channel current setting renders each corresponding diode 226 of the electrode channel forward biased such that voltage at node 240 of the electrode channel is at a voltage equal to the voltage at node 228 of reference channel 202 less a voltage drop across diode 226. The current $I_{ChNReadD}$ is measured for each electrode channel and the current $I_{RefReadD}$ from reference channel 202 is also measured. The current of the reference channel is typically measured for each channel current reading.

Voltage at node 228 of reference channel 202 is set to a 200 V set point voltage or $V_{200VRefsetpoint}$ and voltage at node 228 of all electrode channels are set to a 300 V set point voltage or $V_{300VSetPoint}$. Again, because the actual 200 V reference channel set point voltage may not be exactly equal to 200 V, the 200 V set point voltage is represented by $V_{200VRefSetPoint}$. Similarly, because the actual 300 V electrode channel set point voltage may not be exactly equal to 300 V, the 300 V set point voltage is represented by $V_{300VSetpoint}$. In addition, because the voltage of reference channel 202 is lower than the voltage of the electrode channels, no current flows between the reference channel and any of the electrode channels. The output voltage $V_{ChNReadE}$ of each of the electrode channels is measured.

Lastly, the current of each electrode channel is individually set to a −1.25 µA set point current or $I_{-1.25\ \mu ASetPoint}$ while maintaining voltages at node 240 of all other electrode channels at $V_{300VSetPoint}$. The electrode channel current setting renders each corresponding diode 226 of the electrode channel forward biased such that voltage at node 228 of the electrode channel is at a voltage equal to the voltage at node 228 of reference channel 202 less a voltage drop across diode 226. The voltage $V_{ChNReadF}$ is measured for each electrode channel and the voltage $V_{RefReadF}$ from reference channel 202 is also measured. Note that the voltage of reference channel is typically measured once for all channel current readings.

TABLE I summarizes the calibration steps and the measured voltages and currents of the reference channel and the electrode channels as described above.

TABLE I

| Calibration Steps | Measured Voltage (V) | | Measured Current (µA) | |
|---|---|---|---|---|
| | Reference Channel | Electrode Channel N | Reference Channel | Electrode Channel N |
| (A) Shut off all channels | $V_{RefReadOffset}$ | $V_{ChNReadOffset}$ | $I_{RefReadOffset}$ | $I_{ChNReadOffset}$ |
| (B) Set reference channel to $V_{1kVRefSetPoint}$, electrode channels to $V_{1.2kVRefSetPoint}$ | | $V_{ChNReadB}$ | | |
| (C) Set each electrode channel to $I_{-1.25\mu ASetPoint}$ | $V_{RefReadC}$ | $V_{ChNReadC}$ | $I_{RefReadC}$ | $I_{ChNReadC}$ |
| (D) Set each electrode channel to $I_{-3.75\mu ASetPoint}$ | | | $I_{RefReadD}$ | $I_{ChNReadD}$ |
| (E) Set reference channel to $V_{200VRefSetPoint}$, electrode channels to $V_{300VSetPoint}$ | | $V_{ChNReadE}$ | | |
| (F) Set electrode channels to $I_{-1.25\mu ASetPoint}$ | $V_{RefReadF}$ | $V_{ChNReadF}$ | | |

The reference channel read gain calibration factors for voltage and current, represented by $G_{RefReadV}$, $G_{RefReadI}$, respectively, are known, e.g. calibrated and predetermined at the factory, and utilized in determining various calibration factors and/or offsets. The calibration factors for reading the voltages and currents and the calibration factors and calibration offsets for setting the voltages and currents for each high voltage electrode channel N are shown below as functions of known parameters $G_{RefReadV}$, $G_{RefReadI}$ and measured voltages and currents as listed in TABLE I:

$$G_{ChNReadV} = G_{RefReadV} * (V_{RefReadC} - V_{RefReadF})/(V_{ChNReadC} - V_{ChNReadF})$$

$$G_{ChNReadI} = G_{RefReadI} (I_{RefReadD} - I_{RefReadC})/(I_{ChNReadC} - I_{ChNReadD})$$

$$G_{ChNSetV} = G_{ChNReadV} (V_{ChNReadB} - V_{ChNReadE})/(V_{1.2\ kVSetPoint} - V_{300VSetPoint})$$

$$V_{ChNSetOffset} = V_{300VSetPoint} - (V_{ChNReadE} - V_{ChNReadOffeset}) * (G_{ChNReadV}/G_{ChNSetV})$$

$$G_{ChNSetI} = G_{ChNReadI} * (I_{ChNReadC} - I_{ChNReadD})/(I_{-1.25\ \mu ASetPoint} - I_{-3.75\ \mu ASetPoint})$$

$$I_{ChNSetOffset} = I_{-1.25\ \mu ASetPoint} - (I_{ChNReadC} - I_{ChNReadOffset}) * (G_{ChNReadI}/G_{ChNSetI})$$

where:

$G_{ChNReadV}$ represents the calibration factor for the read voltage gain, i.e. the relation between the reading of voltage 222 and the actual voltage at node 240 for each channel N;

$G_{ChNReadI}$ represents the calibration factor for the read current gain, i.e. the relation between the reading of current 224 and the actual current at node 240 for each channel N;

$G_{ChNSetV}$ represents the calibration factor for the voltage setting gain, i.e. the relation between the setting of the DAC set-point output 214 and the actual voltage at node 240 for each channel N;

$V_{ChNSetOffset}$ represents the offset voltage for setting voltage, i.e., the setting of the DAC set-point output 214 that would result in a 0 voltage at node 240 for each channel N;

$G_{ChNSetI}$ represents the calibration factor for the current setting gain, i.e. the relation between the setting of the DAC set-point output 214 and the actual current at node 240 for each channel N; and $C_{ChNSetOffset}$ represents the offset current for setting current, i.e., the setting of the DAC set-point output 214 that would result in 0 current flow in or out of node 240 for each channel N.

In addition, the calibration factor and the voltage offset for setting the voltage for the reference channel are shown below:

$$G_{RefSetV} = G_{RefReadV} * (V_{RefReadC} - V_{RefReadF})/(V_{1\ kVRefSetPoint} - V_{300VRefSetPoint})$$

$$V_{RefSetOffset} = V_{200VSetPoint} - (V_{RefReadF} - V_{RefReadOffeset}) * (G_{RefReadV}/G_{RefSetV})$$

where:

$G_{RefSetV}$ represents the calibration factor for the reference voltage setting gain, i.e., the relation between the setting of the DAC set-point output 214 and the actual voltage at node 228 for the reference channel; and $V_{RefSetOffset}$ represents the offset voltage for setting reference voltage, i.e., the setting of the DAC set-point output 214 that would result in a 0 voltage at node 228 for the reference channel.

After determining the calibration factors and offsets, the relationships among set point, read back, and output voltages and currents are known. In particular, the actual voltage setting $V_{Set,\ Out}$ can be expressed as a function of the applied voltage setting $V_{Set}$ and the actual current setting $I_{Set,\ Out}$ can be expressed as a function of the applied current setting $I_{Set}$:

Output Voltage = $V_{ChNOut} = (V_{Set} - V_{ChNSetOffset}) * G_{ChNSetV}$

Output Current = $I_{ChNOut} = (I_{Set} - I_{ChNSetOffset}) * G_{ChNSetI}$

In addition, the actual voltage $V_{Read,\ Out}$ for each electrode channel can be expressed as a function of the measured voltage $V_{Read}$ and the actual current $I_{Read,\ Out}$ can be expressed as a function of the measured current $I_{Read}$:

Output Voltage = $V_{ChNOut} = (V_{Read} - V_{ChNReadOffset}) * G_{ChNReadV}$

Output Current = $I_{ChNOut} = (I_{Read} - I_{ChNReadOffset}) * G_{ChNReadI}$

The above-described calibration method is typically generally reduced to generating a first electrical reference input at the reference channel and a first electrical source input at each of the electrode or source channels. A first electrical value at each of the reference and electrode channels are measured. A second electrical reference input at the reference channel and a second electrical electrode input at each of the electrical electrode channels are then generated, the second inputs being different from the corresponding first inputs. A second value at each of the reference and electrical electrode channels are then measured. Each electrical input and each measured value are optionally a voltage and/or a current.

A readout calibration factor, e.g., $G_{ChNReadV}$ or $G_{ChNReadI}$, is typically determined as a function of a ratio of differences between the first measured reference value and the first measured electrode value and between the second measured reference value and the second measured electrode value.

All electrode and reference channels are optionally shut off and an offset voltage and current at each of the reference and electrode channels are measured. A calibration offset value, e.g. $V_{ChNSetOffset}$ or $I_{ChNSetOffset}$, is typically determined as a function of the measured offset voltages and currents. In addition, a setting calibration offset $V_{ChNSetOffset}$ and $I_{ChNSetOffset}$ are preferably determined as a function of one of the reference inputs and as a function of a difference between one of the measured electrode channel values and one of the measured offset source channel values.

An input setting reference calibration offset, e.g., $V_{RefsetOffset}$, is typically determined as a function of one of the reference inputs and a function of a difference between one of the measured reference channel values and one of the measured offset reference channel values.

A setting calibration factor, e.g., $G_{ChNSetV}$ or $G_{ChNSetI}$, is typically determined as a function of a ratio of differences between the first measured reference value and the second measured reference value and between the first reference input and the second reference input.

A setting reference offset, e.g., $G_{RefSetV}$, is typically determined as a function a ratio of differences between the first measured reference value and the second measured reference value and between the first reference input and the second reference input.

In the calibration process described above, the voltage drop across each of diodes 226 is assumed to be constant at constant current flow such that the diode voltage drops do not have a significant effect on the calibration process because each pair of calibration points is performed at the same bias currents of −1.25 μA. In addition, the offset calibration is not affected by the diode voltage drops because the offset calibration is performed by shutting off all high voltage sources of the reference and electrode channels.

Furthermore, the above-described calibration process calibrated a slope of voltage output versus voltage setting assuming a similar voltage drop across each of diodes 226. The process also ensures against a large voltage difference between the electrode channels during calibration. A large voltage difference between the electrode channels during calibration can generate undesired fluid flow in the microfluidic chip, degrading accuracy and performance.

As noted above, any other suitable calibration processes may be utilized and numerous modifications can be optionally made to achieve similar calibration results. For example, the above described calibration process is a two point calibration process such that the process inherently assumes that the circuit components behave linearly, i.e., the circuit components are highly linear and have low voltage coefficients. To compensate for non-linearity circuit components, the above described calibration process may be expanded to perform multiple point calibration for one or more of the calibration factors.

While the above is a complete description of preferred embodiments of the invention, various alternatives, modifications, and equivalents can be used. It should be evident that the invention is equally applicable by making appropriate modifications to the embodiments described above. Therefore, the above description should not be taken as limiting the scope of the invention that is defined by the metes and bounds of the appended claims along with their full scope of equivalents.

What is claimed is:

1. A method of calibrating a plurality of electrical source channels, comprising:

generating a first electrical reference signal at a reference channel;

applying the first electrical reference signal to each of the electrical source channels to generate a first electrical source signal at each of the electrical source channels;

measuring a first electrical value at each of the reference and electrical source channels;

generating a second electrical reference signal at the reference channel;

applying the second electrical reference signal to each of the electrical source channels to generate a second electrical source signal at each of the electrical source channels, the second electrical reference signal and the second electrical source signal being different from the first electrical reference signal and the first electrical source signal, respectively;

measuring a second electrical value at each of the reference and electrical source channels; and determining a readout calibration factor for each of the electric source channels as a function of a ratio of differences between the first and second measured reference values and between the first and second measured source values.

2. The method of calibrating according to claim 1, wherein each of the first and second reference and source signals and the first and second measured reference and source values is selected from the group consisting of voltage and current.

3. The method of calibrating according to claim 1, further comprising determining a setting calibration factor for each electrical source channel as a function of a ratio of differences between the first and the second measured electrical values for each electrical source channel and between the first and the second electrical reference signals.

4. The method of calibrating according to claim 1, further comprising determining a setting reference offset as a function a ratio of differences between the first and the second measured reference values and between the first and the second setting electrical reference signals.

5. The method of calibrating according to claim 1, further comprising:

shutting off all source channels and reference channel;

measuring an offset voltage and current value at each of the reference and source channels; and determining a calibration offset value as a function of the measured offset voltages and currents.

6. The method of calibrating according to claim 5, further comprising determining a setting calibration offset as a function of one of the reference signals and a function of a difference between one of the measured source channel values and one of the measured offset source channel values.

7. The method of calibrating according to claim 5, further comprising determining a setting reference calibration offset as a function of one of the reference signals and a function of a difference between one of the measured reference channel values and one of the measured offset reference channel values.

8. A method for direction of material in a fluidic chip, the chip including at least one fluidic channel extending between two electronic contact points, each contact point adapted to be in contact with an electrical source channel, comprising:

calibrating the electrical source channels using a reference channel; and applying an electrical direction signal to at least one of said electrical source channels using results of said calibrating, wherein said calibrating comprises:

generating a first electrical reference signal at the reference channel;

applying the first electrical reference signal to each of the electrical source channels to generate a first electrical source signal at each of the electrical source channels;

measuring a first electrical value at each of the reference and electrical source channels;

generating a second electrical reference signal at the reference channel;

applying the second electrical reference signal to each of the electrical source channels to generate a second electrical source signal at each of the electrical source channels, the second electrical reference signal and the second electrical source signal being different from the first electrical reference signal and the first electrical source signal, respectively;

measuring a second electrical value at each of the reference and electrical source channels; and determining a readout calibration factor for the electric source channels as a function of a ratio of differences between the first and second measured reference values and between the first and second measured source values.

9. The method for direction of material in a fluidic chip according to claim 8, wherein each of the first and second reference and source signals and the first and second measured reference and source values is selected from the group consisting of voltage and current.

10. The method for direction of material in a fluidic chip according to claim 8, further comprising determining a setting calibration factor for each electrical source channel as a function of a ratio of differences between the first and the second measured electrical values for each electrical source channel and between the first and the second electrical reference signals.

11. The method for direction of material in a fluidic chip according to claim 8, further comprising determining a setting reference offset as a function a ratio of differences between the first and the second measured reference values and between the first and the second setting electrical reference signals.

12. The method for direction of material in a fluidic chip according to claim 8, further comprising:

shutting off all source channels and reference channel;

measuring an offset voltage and current value at each of the reference and source channels; and determining a calibration offset value as a function of the measured offset voltages and currents.

13. The method for direction of material in a fluidic chip according to claim 12, further comprising determining a setting calibration offset as a function of one of the reference signals and a function of a difference between one of the measured source channel values and one of the measured offset source channel values.

14. The method for direction of material in a fluidic chip according to claim 12, further comprising determining a setting reference calibration offset as a function of one of the reference signals and a function of a difference between one of the measured reference channel values and one of the measured offset reference channel values.

* * * * *